United States Patent [19]

Koster et al.

[11] Patent Number: 5,420,277

[45] Date of Patent: May 30, 1995

[54] INTERMEDIATES FOR THE PREPARATION OF HETEROARYL DERIVATIVES OF MONOCYCLIC BETA-LACTAM ANTIBIOTICS

[75] Inventors: William H. Koster, Pennington, N.J.; Joseph E. Sundeen, Yardley, Pa.; Henner Straub, Regensburg, Germany; Peter Ermann, Donaustauf, Germany; Uwe D. Treuner, Etterzhausen, Germany; Kent Amsberry; Michael Fakes, both of East Windsor, N.J.; Sailesh A. Varia, Plainsboro, N.J.

[73] Assignee: E. R. Squibb & Sons, Inc., Princeton, N.J.

[21] Appl. No.: 157,801

[22] Filed: Nov. 29, 1993

Related U.S. Application Data

[60] Division of Ser. No. 941,600, Sep. 18, 1992, Pat. No. 5,290,929, which is a continuation-in-part of Ser. No. 608,945, Nov. 5, 1990, abandoned.

[51] Int. Cl.$^6$ .................. C07D 241/44; C07D 491/04
[52] U.S. Cl. .................... 544/345; 544/229; 544/337; 544/354; 544/355; 560/160; 564/443
[58] Field of Search ............... 544/345, 354, 355, 229

[56] References Cited

U.S. PATENT DOCUMENTS

| | | | |
|---|---|---|---|
| 5,037,983 | 8/1991 | Sundeen et al. | 544/355 |
| 5,250,691 | 10/1993 | Straub et al. | 544/355 |
| 5,290,929 | 3/1994 | Koster et al. | 540/355 |

FOREIGN PATENT DOCUMENTS

| | | |
|---|---|---|
| 304158 | 2/1989 | European Pat. Off. |
| 420069 | 4/1991 | European Pat. Off. |

OTHER PUBLICATIONS

Koster et al, *Chemical Abstracts*, vol. 117, No. 90045 (Abstract for EP484881, May, 13 1992) (1993).
Budesinsky et al, *Collection Czechoslov. Chem. Commun.* 36, pp. 2527–2539 (1971).

*Primary Examiner*—Emily Bernhardt
*Attorney, Agent, or Firm*—Ellen K. Park

[57] ABSTRACT

Antibacterial activity is exhibited by novel compounds having the formula

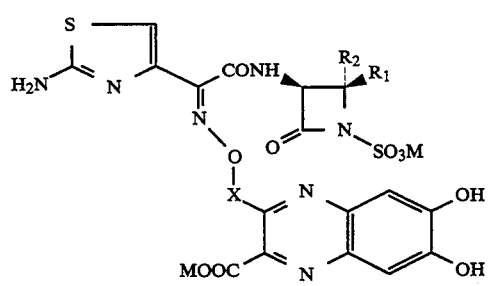

where $R_1$, $R_2$, and M are as defined herein and X is —$(CH_2)_n$— wherein n is 0, 1, 2, 3 or 4 or $CR_3R_4$ wherein $R_3$ and $R_4$ are the same or different and each is hydrogen, —$CH_3$ or —$C_2H_5$ or $R_3$ and $R_4$ taken together with the carbon atom to which they are attached form a 3, 4, 5, 6 or 7-membered cycloalkyl ring. Also described are various intermediates for the preparation of compounds of formula 1.

7 Claims, No Drawings

INTERMEDIATES FOR THE PREPARATION OF HETEROARYL DERIVATIVES OF MONOCYCLIC BETA-LACTAM ANTIOBIOTICS

This is a division of application Ser. No. 07/941,600, filed Sep. 18, 1992, now U.S. Pat. No. 5,290,929, which is a continuation-in-part of U.S. Ser. No. 07/608,945, filed Nov. 5, 1990, now abandoned.

BRIEF DESCRIPTION OF THE INVENTION

Compounds having the formula

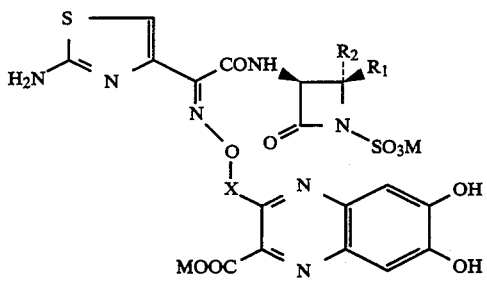

having antibacterial activity are described herein. In formula 1, and throughout the specification, the symbols are as defined below.

$R_1$ and $R_2$ are the same or different and each is hydrogen, alkyl, alkenyl, alkynyl, cycloalkyl, phenyl, substituted phenyl or a 4, 5, 6 or 7-membered heterocycle (hereinafter referred to as $R_a$), or one of $R_1$ and $R_2$ is hydrogen and the other is azido, halomethyl, dihalomethyl, trihalomethyl, alkoxycarbonyl, phenylethyl, 2-phenylethenyl, 2-phenylethynyl, carboxyl, —CH$_2$X$_1$ [wherein $X_1$ is azido, amino, hydroxy, carboxyl, alkoxycarbonyl, alkanoylamino, phenylcarbonylamino, (substituted phenyl) carbonylamino, alkylsulfonyloxy, phenylsulfonyloxy, (substituted phenyl) sulfonyloxy, phenyl, substituted phenyl, cyano,

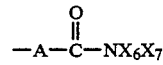

—S—X$_2$, or —O—X$_2$ wherein A, X$_2$, X$_6$ and X$_7$ are as hereinafter defined], —S—X$_2$ or —O—X$_2$ [wherein X$_2$ is alkyl, substituted alkyl, phenyl, substituted phenyl, phenylalkyl, (substituted phenyl)alkyl, formyl, alkanoyl, substituted alkanoyl, phenylalkanoyl, substituted phenylalkanoyl, phenylcarbonyl, substituted phenylcarbonyl, heteroaryl, heteroarylalkyl, heteroarylalkanoyl or heteroarylcarbonyl, and in the case of when $X_1$ is —O—X$_2$ then X$_2$ can also be alkylideneamino, alkanoylamino, carboxyalkylideneamino, alkylsulphinylamino, alkoxycarbonyl or alkylsulphonylamino. In addition $R_1$ and $R_2$ can be

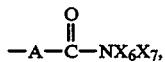

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, substituted phenylcarbonyl, phenylalkylcarbonyl, substituted phenylalkylcarbonyl, carboxyl, alkoxycarbonyl, aminocarbonyl, substituted aminocarbonyl, or cyano] or

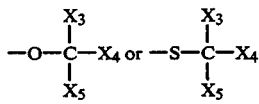

[wherein A is —CH=CH—, —(CH$_2$)$_m$—, —(CH$_2$)$_m$—O—, —(CH$_2$)$_m$—NH—, or —CH$_2$—S—CH$_2$—, where m is 0, 1 or 2, and X$_6$ and X$_7$ are the same or different and each is hydrogen, alkyl, phenyl or substituted phenyl, or X$_6$ is hydrogen an X$_7$ is amino, substituted amino, alkanoylamino or alkoxy, or X$_6$ and X$_7$ when taken together with the nitrogen atom to which they are attached form a 4, 5, 6 or 7-membered heterocycle];

X is —(CH$_2$)$_n$— wherein n is 0 or an integer of 1 to 4 or CR$_3$R$_4$ wherein R$_3$ and R$_4$ are the same or different and each is hydrogen, —CH$_3$ or —C$_2$H$_5$ or R$_3$ and R$_4$ taken together with the carbon atom to which they are attached form a 3, 4, 5, 6 or 7-membered cycloalkyl ring; M is hydrogen, tetraalkylammonium, sodium, potassium or any other cation capable of forming a pharmaceutically acceptable salt.

Preferred compounds are when X is —CH$_2$—. The preferred compound is illustrated in Examples eleven and twenty. The compounds of this invention are pictured as acids or salts. They can also exist, however, as zwitterions (internal or inner salts), and these are also included within the language "pharmaceutically acceptable salts" and the scope of this invention. Further, it is intended that amino acid salts such as L-arginine and L-lysine are within the scope of "pharmaceutically acceptable salts."

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "cycloalkyl" refers to cycloalkyl groups having 3, 4, 5, 6 or 7 carbon atoms.

The term "substituted alkyl" refers to alkyl groups substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, R$_a$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The term "substituted alkanoyl" refers to alkanoyl groups substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsufinyl or alkylsulfonyl groups.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_a$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy or 1 to 4 carbons, alkylsulfonyl, phenyl, substitued phenyl, 2-furfurylideneamino

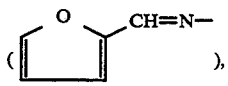

benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substitued and unsubstituted pyridinyl, furanyl, pyrrolyl, thienyl, 1, 2, 3-triazolyl, 1,2,4-triazolyl, imidazolyl, thiazolyl, thiadiazolyl, pyrimidinyl, oxazolyl, triazinyl and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2, 3 -dioxo -1 -piperazinyl.

The term "substituted amino" refers to a group having the formula —$NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy or amino.

DETAILED DESCRIPTION OF THE INVENTION

The β-lactams of formula 1 have activity against gram-positive and gram-negative organisms. Of particular interest is the good activity against gram negative organisms in vitro and in vivo exhibited by the compounds of this invention. The compound of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The compounds of this invention can be prepared by coupling a compound having the formula

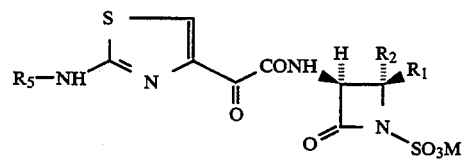

wherein $R_5$ is hydrogen or a suitable protecting group such as formyl or trityl with a compound of the formula

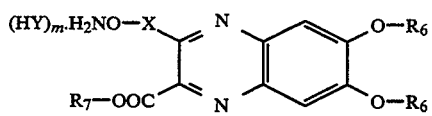

wherein $R_6$ is hydrogen or a suitable phenol-protecting group or $R_6/R_6$ is a catechol protecting group such as Si(t-butyl)$_2$, $R_7$ is hydrogen or a suitable protecting group such as t-butyl or diphenylmethyl and HY is a mineral acid, sulfonic acid or another non-nucleophilic acid capable of forming a stable hydroxylamine salt and m is 0, 1, or 2 or fractions of 1 or 2. All synthesis of compounds using intermediates carrying protecting groups such as $R_5$, $R_6$, and $R_7$ in formulae 2, 3 and 6 provide protected derivatives of 1 which must be finally deprotected.

Alternatively, the compounds of formula 1 can be prepared by reacting a compound of the formula

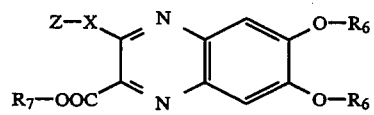

wherein Z is a leaving group such as halogen, trifluoroacetate, alkylsulfonate, arylsulfonate or other activated esters of alcohols; wherein $R_6$ is the same as above with the proviso that if $R_5$ is trityl then $R_6$ may also be benzyl or another protecting group which can be removed by catalytic hydrogenation and $R_7$ is the same as above with the proviso that in compound 4, $R_7$ may also be allyl, trimethylsilylethyl or other non-sterically crowded carboxyl protecting group with a compound of the formula

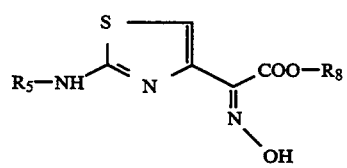

wherein $R_5$ is a defined above and $R_8$ is hydrogen or a carboxyl protecting group which can be removed under conditions wherein $R_7$ remains inert. If $R_5$ is trityl then $R_8$ may also be p-nitrobenzyl to form a compound of the formula

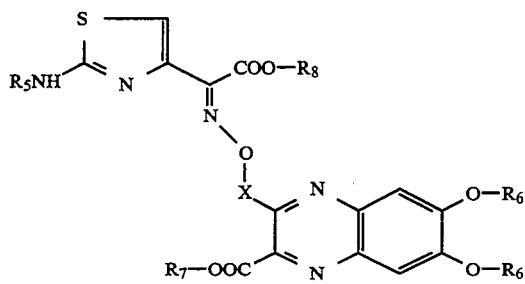

wherein $R_5$, $R_6$, $R_7$ and $R_8$ have hereinbefore been defined. Compound 6 is then reacted with a compound of the formula

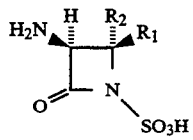

to form compounds of the invention represented by formula 1.

Compound 6 can also be formed by reacting compound 3 with a compound of the formula

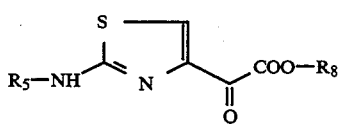

wherein $R_5$ and $R_8$ are as hereinbefore defined.

Compound 3 can be prepared from compound 9 by total or partial removal of the protecting groups $R_6$, $R_7$, $R_9$, $R_{10}$.

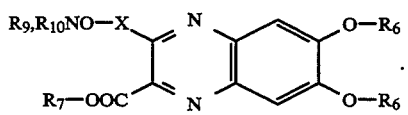

Also, the cyclic hydroxamic acids of formula 10 can be hydrolyzed (HCl conc., ca 80°) to form the hydroxylamines of formula 3.

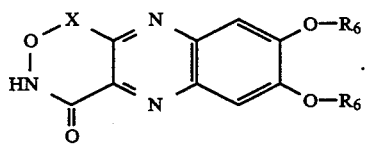

Alternatively, compound 3 can be prepared from compound 11 by desoxygenation and total or partial removal of the protecting group $R_6$, $R_7$, $R_9$, $R_{10}$.

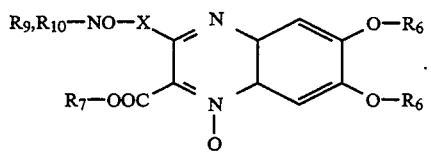

Compounds 9 and 11 can be prepared by reacting a compound of formula 12, with a N-protected derivative of hydroxylamine of the formula 13 in an organic solvent and in the presence of a base such as $K_2CO_3$ or triethylamine.

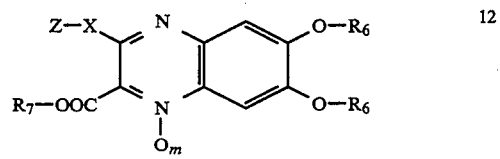

In the case of m=0 formula 12 is identical with formula 4. Hence, all definitions of $R_6$, $R_7$, X and Z are specified as in formula 4. Instead of activated esters of alcohols as leaving groups Z, the alcohols themselves (Z=OH) can be used if the alcohols are preactivated by using e.g. Mitsunobu conditions ($PPh_3$/DEAD/THF).

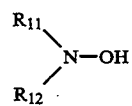

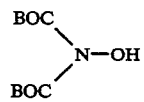

In formula 13, $R_{11}$ and $R_{12}$ are combinations of suitable protecting groups such as H, t-butyloxy-carbonyl (BOC), benzyloxy-carbonyl or $R_{11}$ and $R_{12}$ taken together form a divalent, cyclic protective group such as isopropylidene group $(CH_3)_2C$ or a phthalyl group. In the case of $R_{11}=R_{12}=BOC$ ($(BOC)_2NOH$) compound 13a is novel and forms an integral part of this invention. In formula 9 and 11, $R_9$ and $R_{10}$ are equivalent to $R_{11}$ and $R_{12}$ in formula 13.

Compound 13a is made by reacting a compound of the formula 14

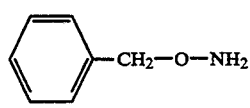

with di-t-butyldicarbonate in a mixture of water, tetrahydrofuran (THF) and NaOH to form a compound of the formula 15. Intermediate 15 is also reported in the literature: R. Sulsky and J. P. Demers, Tetrahedron Letters, 30, (1989), 31–34.

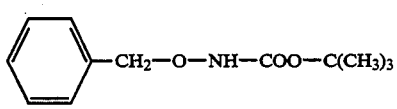

Compound 15 is reacted with di-t-butyldicarbonate in tetrahydrofuran and 4-dimethylaminopyridine to form a compound of the formula 16.

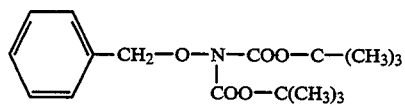
16

Compound 16 is hydrogenated in the presence of palladium on activated carbon to form compound 13a.

Compound 12 can be prepared by halogenation (e.g. NBS) of the corresponding alkyl substituted compound 17.

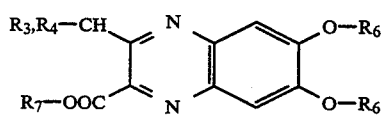
17 wherein $R_3$, $R_4$ is defined previously or by conversion of the correponding N-oxides of the formula 18 with acetylchloride or trifluoroacetic anhydride. The acetate group introduced in this manner is subsequently displaced by halide ion and in the case when m is one in formula 18 the remaining N-oxide moiety is deoxygenated to afford a compound of formula 12.

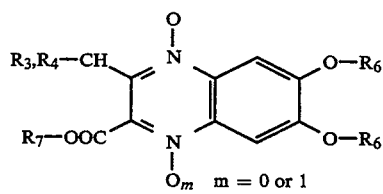
18

In order to prepare compounds of formula 1 when n is zero, compounds of formula 4 wherein Z is halogen and X is a single bond are prepared by reacting compounds of the formula

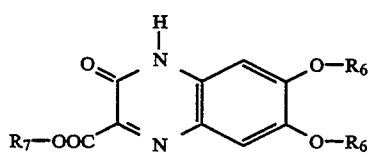
18a with $POCl_3$. A compound of formula 18a is equivalent to a compound of formula 4 when Z is OH and n is zero.

Alternatively, compound 12 can be prepared by conversion of the Z—X group in 12 to a modified Z'—X' group as exemplified in the following Scheme 1 and Scheme 2. Formula 19 is identical with formula 12 if Z=Hal, X=$CH_2$ and m=0; formula 19 is also identical with formula 4 if Z=Hal and X=$CH_2$.

Scheme 1

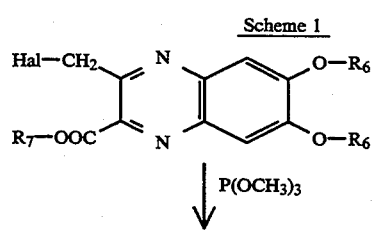
19

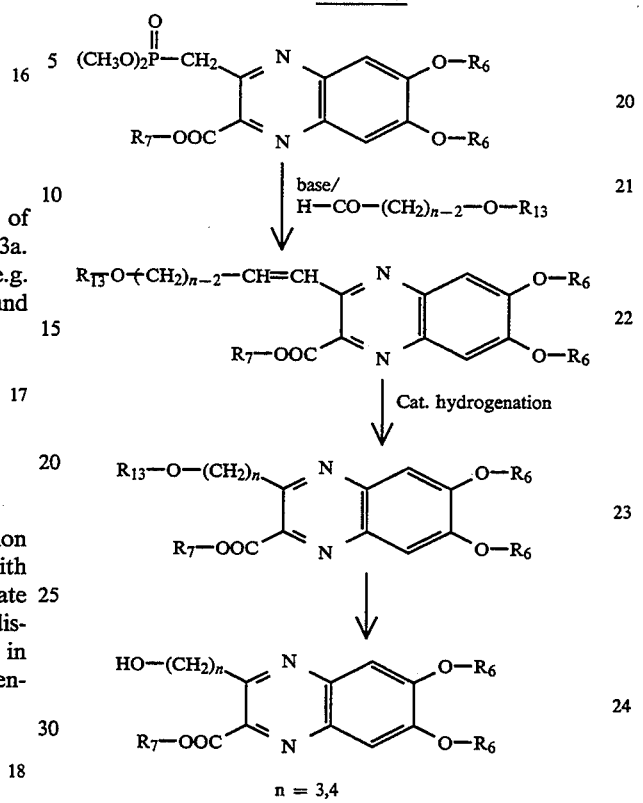

n = 3,4

Formula 24 is identical with formula 4 if Z=OH and X=$(CH_2)_n$.

Aldehydes 21 (n=3,4) with suitable protective groups $R_{13}$ such as acetate, benzyl etc. are known from the literature. Alternatively, compound 22 can be prepared via the following scheme 2.

Scheme 2

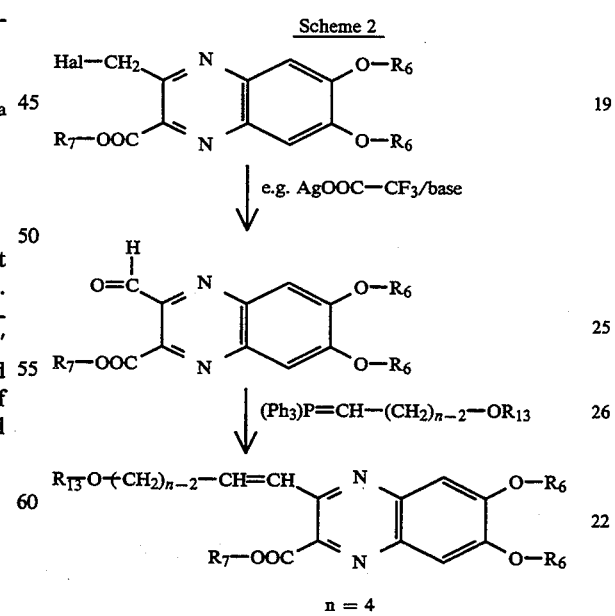

n = 4

The necessary Wittig reagent 26 (n=4) with a suitable protective group $R_{13}$, such as benzyl, is known from the literature.

Alternatively, compound of formula 12 with m=0 and Z=OR$_{13}$ or H can be prepared by reacting a compound of formula 27 wherein X is CR$_3$R$_4$ or (CH$_2$)$_n$; n=1,2,3,4 (as defined previously) and Z is hydrogen or a suitable protected hydroxy group (as defined previously) with

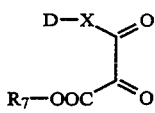

a compound of formula 28 wherein R$_6$ is a suitable phenol-protecting group (as defined previously) or R$_6$/R$_6$ is a catechol protecting group (as defined previously).

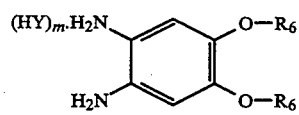

Instead of compound of the formula 27, derivatives thereof such as hydrates or bisulfite adducts can be used. Compound of formula 27 can be prepared from compounds of the formula 29 by direct oxidation (e.g. by means of SeO$_2$) or by indirect oxidation (e.g. nitrosation followed by treatment with N$_2$O$_4$ or condensation with dimethoxy dimethylamino methane followed by ozonolysis).

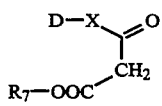

X=CR$_3$R$_4$; (CH$_2$)$_n$; n=1,2,3,4
D=H, OR$_{13}$
R$_7$=as defined previously Compounds of formula 28 can be prepared by reduction of corresponding dinitro compounds as exemplified for the isopropylidene-protected derivative 28 (R$_6$/R$_6$=C(CH$_3$)$_2$) in U.S. Pat. No. 4,904,757, Example 3D.

Alternatively, compound 28 can be prepared by reduction of a protected amino-nitro-catechol as exemplified for the dibenzyl protected derivative 33 (24, R$_6$=CH$_2$—C$_6$H$_5$) in scheme 3.

Scheme 3

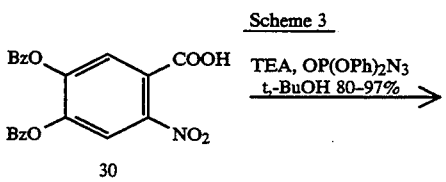

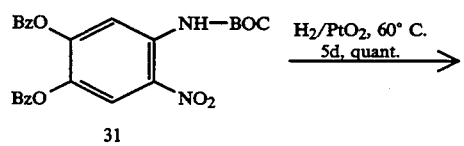

-continued
Scheme 3

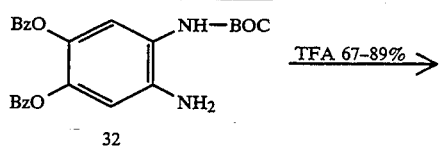

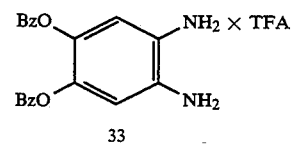

The dibenzyl confound 33 is novel and forms an integral part of this invention.

Compound 18 with m=1 can be prepared by oxidation of compound 17 by means of peroxy acids or by reacting a compound of formula 34 (wherein R$_6$ is defined as previously) with a compound of formula 29 (wherein X and D are defined as previously).

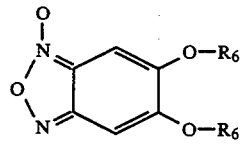

Compound 34 can be prepared by reacting compound 35 with NaN$_3$ in dimethyl sulfoxide.

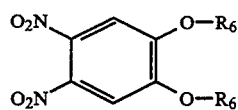

The isopropylidene-protected derivative 35 (R$_6$/R$_6$=C(CH$_3$)$_2$) is disclosed in U.S. Pat. No. 4,904,775. Replacement of the isopropylidene protecting group by other protecting groups can be achieved by hydrolysis removal (HCl conc./80° C.) of the isopropylidene group and subsequent protection of 4,5-dinitrocatechol with another phenol/or catechol-protecting group. Obviously, such a replacement of a protective group by another protective group R$_6$ can also be performed on a later stage of the synthesis as exemplified by the following scheme 4.

Scheme 4

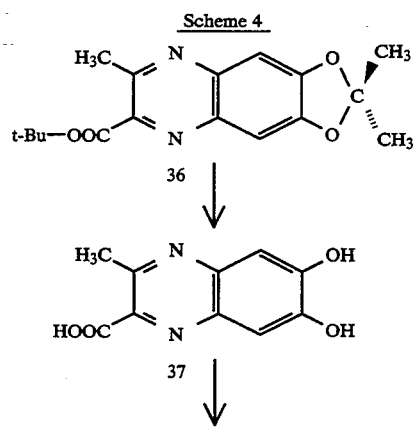

-continued
Scheme 4

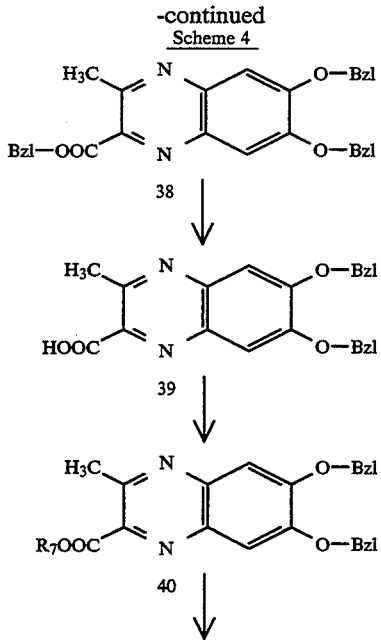

The preferred method of preparation for the preferred compound of Example 20 involves the following sequence.

Examples 20A→20B→21 →3→8→9→20H→20I.

The compounds of formula 1 contain at least one chiral center-the carbon atom (in the 3-position of the β-lactam nucleus) to which the acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephalosporins (e.g., cephalosporin C).

The compounds of formula 1 have the imino substituent

and can, therefore, exist as the syn or anti isomer or as a mixture of isomers. All of these isomeric forms are within the scope of this invention. In general, however, the syn isomer of a compound of formula 1 has the greatest activity.

The freeze dried or lyophilized L-arginine salts of the compounds of formula I are prepared by mixing the required amount of the formula I compound and 90% of the required L-arginine together. For example, for a 1 gram sample of the compound ([2R-[2α,3α(Z)]]-3-[[[[1-(2-amino-4-thiazolyl)-2-[(2-methyl-4-oxo-1-sulfo-3-azetidinyl)-amino]-2-oxoethylidene]amino]oxy]methyl]-6,7-dihydroxy-2-quinoxalinecarboxylic acid) the required amount of L-arginine is 0.58 to 0.65 grams to bring the pH of the solution to preferably about 5.5. Alternatively, based on in-process titration, 100% of the L-arginine required for preparation is used to bring the pH of the solution to about 5.5. This solution is prepared by dissolving the dry mixture of the formula I compound and L-arginine in about 90% of the required amount of water. After the pH has been adjusted to preferably about 5.5 with more L-arginine, if required, the solution is brought to final volume with water. The solution is clarified and filtered, if required. The solution is then freeze dried by conventional methods. Similar methods known to those skilled in the art may be utilized to form other amino acid salts of the compounds of formula I.

The following examples are specific embodiments of this invention.

EXAMPLE 1 t-Butyl-2,3-dioxobutyrate

The above compound was prepared according to the procedure described by H. Dahn, H. Cowal and H. P. Schlunke, Helv. Chim. Acta. 53, 1598 (1970) by oxidation ($N_2O_4$) of t-butyl-2-oximino-3-oxo-butyrate. M.P. 62°–66° C.

EXAMPLE 2

2,2,7-Trimethyl-1,3-dioxolo-[4,5-g]-quinoxaline-6-carboxylic acid, 1,1-dimethylethyl ester

[5,6-diamino-2,2-dimethyl-1,3-benzodioxole; dihydrochloride salt] (U.S. Pat. No. 4,904,775, Example 3D) (6.8 g, 0.02 mmol) was dissolved in a mixture of 25 ml water and 10 ml tetrahydrofuran and the pH of the solution was adjusted to 5.5 by the addition of 2N NaOH. After addition of the compound from Example 1 (3.8 g; 0.02 mol) the mixture was refluxed for 2 hours, concentrated in vacuo to remove the organic solvent tetrahydrofuran and then extracted with ethyl acetate. The combined organic phases were washed with brine, dried ($Na_2SO_4$) and then evaporated in vacuo to leave an oil which crystallized by the addition of petroleum ether.

M.P. 104°–105° C.; yield 5.2 g (82%). $C_{17}H_{20}N_2O_4$ % C calc. 64.54%, found 64.40% % H calc. 6.37%, found 6.41% % N calc. 8.85%, found 8.86% IR(KBr): 1710 $cm^{-1}$; $^1H$-NMR(DMSO-$d_6$): δ=1.65 (s, 9H); 1.81 (s, 6H); 2.73 (s, 3H) 7.34 (s, 1H); 7.42 (s, 1H) ppm; $^{13}C$-NMR(DMSO-$d_6$): δ=21.95 (q); 25.28 (q); 27.46 (q); 82.22 (s); 102.94 (d); 103.50 (d); 120.43 (s); 137.24 (s); 140.28 (s); 142.50 (s); 147.94 (s); 150.16 (s); 151.43 (s); 164.61 (s).

EXAMPLE 3

7-Bromomethyl-2,2-dimethyl-1,3-dioxolo-[4,5-g]-quinoxaline-6-carboxylic acid, 1,1-dimethylethyl ester To a solution of the compound from Example 2 (7.8 g, 24.6 mmol) in 150 ml dry tetrachloromethane, N-bromosuccinimide (4.38 g, 24.6 mmol) and a trace of azobisisobutylronitrile (AiBN) were added and the suspension was refluxed for 3 hours. Over this period of time, small additional quantities of the catalyst (AiBN) were added. After cooling, the formed succinimide was filtered off (2.1 g) and the filtrate was evaporated in vacuo to leave an oil which was chromatographed on silica gel eluting with ethylacetate/toluene (1:6). Evaporation of the relevant fractions yielded the corresponding dibromo derivative (0.8 g; 7%) as side product, the desired monobromo compound (6.5 g, 67%) as main product and recovered starting material (1.8 g; 23%). Recrystallization of the monobromo compound from petroleum ether (bp 60°–80° C.) containing a trace of ethyl acetate afforded a pure sample of title compound; m.p. 130.5° C.–131.5° C.; yield 4.85 g (50%).

IR(KBr): 1728 cm$^{-1}$; $^1$H-NMR(DMSO-d$_6$): $\delta$=1.63 (s, 9H); 1.81 (s, 6H); 4.97 (s, 2H) 7.41 (s, 1H); 7.48 (s, 1H) ppm; $^{13}$C-NMR(DMSO-d$_6$): $\delta$=24.16 (q); 27.43 (q); 31.82 (t); 82.91 (s); 103.14 (d); 103.63 (d); 121.18 (s); 138.62 (s); 140.13 (s); 141.53 (s); 146.98 (s); 151.59 (s); 152.24 (s), 163.53 (s) ppm.

EXAMPLE 4 t-Butyl-N-benzyloxycarbamate

To a stirred solution of O-benzylhydroxylamine (16.0 g; 0.13 mol) and di-t-butyldicarbonate (28.4 g; 0.13 mol) in a mixture of water (150 ml) and tetrahydrofuran (150 ml) 2N NaOH solution was added dropwise to adjust the pH to 8–9 and this pH was maintained for an additional 2 hours by occasional addition of 2N NaOH. After extraction with ethylacetate the combined organic layers were washed with brine, dried (MgSO$_4$) and evaporated in vacuo to leave an oil which was used in the next example without any further purification; yield 29 g (100%).

EXAMPLE 5

(Phenylmethoxy)imidodicarbonic acid, bis(1,1-dimethylethyl) ester

To a stirred solution of the compound of Example 4 (29 g; 0.13 mol) triethylamine (27.9 ml; 0.2 mol) and 4-dimethylamino-pyridine (trace) in dry tetrahydrofuran (200 ml) a solution of di-t-butyl dicarbonate (39.7 g; 0.18 mol) in 20 ml dry tetrahydrofuran was added dropwise at a rate that temperature did not exceed 40° C. Stirring was continued at this temperature (40° C.) for additional 30 minutes and then at room temperature overnight. The mixture was taken up in ether, washed with buffer solution pH=4 (citrate) and brine, dried (MgSO$_4$) and evaporated in vacuo. From the oily residue (still containing few ml of ether) the title compound was crystallized by cooling to 0° C.; m.p. 77.5°–78.5° C.; yield 70.4%; an analytical sample was recrystallized from petroleum ether (bp 40°–60° C.); m.p. 77.5°–78.5° C. C$_{17}$H$_{25}$NO$_5$% C calc. 63.14%, found 63.14% % H calc. 7.79%, found 7.82% % N calc. 4.33%, found 4.35% IR(KBr): 1755 1730cm$^{-1}$: $^1$H-NMR(DMSO-d$_6$): $\delta$=1.49 (s, 18H); 4.88 (s, 2H), 7.42 (s, 5H)ppm.

EXAMPLE 6

Hydroxyimidodicarbonic acid, bis(1,1-dimethylethyl)ester

A solution of the compound of Example 5 (8.09 g, 0.025 mol) in ethanol (150 ml) was hydrogenated in the presence of palladium (10%) on activated carbon (3.5 g). After 15 minutes the hydrogenation was completed (monitored by thin layer chromatography), the catalyst was removed by suction and the filtrate was evaporated in vacuo. The oily residue solidified by stirring with pentane; m.p. 88.5°–89.5° C., yield 71.2%; an analytical sample was recrystallized from petroleum ether (60°–70° C.); m.p. sint 88.7° C., 91°–92° C.

C$_{10}$H$_{19}$NO$_5$% C calc. 51.49%, found 51.48% % H calc. 8.21%, found 8.21% % N calc. 6.00%, found 6.02% IR(KBr): 1775 1752, 1685cm$^{-1}$ $^1$H-NMR(DMSO-d$_6$): $\delta$=1.48 (s, 18H); 9.95 (s, 1H).

EXAMPLE 7

(2R-cis)-3-[[[2-(Formylamino)-4-thiazolyl]-oxoacetyl-]amino]-2-methyl-4-oxo-1-azetidine-sulfonic acid, N,N,N-tributyl-1-butanammonium salt To a suspension of (2R-cis)-3-[[[2-(Formylamino)-4-thiazolyl]-oxoacetyl]amino]-2-methyl-4-oxo-1-azetidine-sulfonic acid, monopotassium salt as described in Example 16A (10.0 g; 0.025 mol) in water (250 ml) tetrabutylammoniumhydrogensulfate (9.33 g; 0.027 mol) was added and the pH was adjusted to 5.5–6.0 by the addition of 2N KOH. The mixture was extracted thrice with chloroform (100 ml, 60 ml, 60 ml) and the combined organic layers were washed with few ml water, dried (MgSO$_4$) and evaporated in vacuo to leave a viscous foam which solidified by stirring with petroleum ether (bp 60°–80° C.); the solid was collected by suction and dried in vacuo over P$_2$O$_5$; mp=82°–88.5° C. dec; yield 11.6 g (77%). C$_{26}$H$_{45}$N$_5$O$_7$S$_2$ % C calc. 51.72%, found 50.96% % H calc. 7.51%, found 7.61% % N calc. 11.60%, found 11.30% % N calc. 10.62% found 10.40%

IR(KBr): 1760 cm$^{-1}$; $^1$H-NMR(DMSO-d$_6$): $\delta$=0.89 (t, 12H); 1.22 (d, 3H; J=7 Hz); 1.15–1.75 (m, 16H); 3.00–3.25 (m, 8H); 4.02 (quin(ps), 1H, J'=6 Hz); 5.05 (d,d, 1H, J'=6 Hz, J''=8.5 Hz); 8.41 (s, 1H); 8.54 (s, 1H); 9.60 (d, 1H, J''=8.5 Hz); 12.68 (s, 1H).

EXAMPLE 8

7-[[[Bis[1,1-dimethylethoxy)carbonyl]amino-oxy-]methyl]-2,2-dimethyl-1,3-dioxolo[4,5g]-quinoxaline-6-carboxylic acid, 1,1-dimethylethyl ester Finely ground potassium carbonate (2.71 g; 19.6 mmol), N,N-diBOC-hydroxylamine (title compound of Example 6) (1.43 g; 6.13 mmol) and a trace of sodium iodide were added to a suspension of the compound of Example 3 (1.94 g; 4.9 mmol) and stirring was continued for 3 hours at room temperature. The solvent was removed in vacuo and the residue was taken up in ethyl acetate, washed twice with buffer solution pH 3 (citrate) and, dried (Na$_2$SO$_4$). Evaporation of the solvent in vacuo yielded an oil (4.4 g) which was purified chromatographically on silicagel eluting with ethyl acetate/toluene (1:3). The relevant fractions were combined, evaporated in vacuo to leave the title compound as an oil, which was used in the next step without any additional purification. yield 2.21 g (92%); mp=91°–94° C. (from hexane).

IR(film): 1790, 1750–1710 cm$^{-1}$ $^1$H-NMR(DMSO-d$_6$): $\delta$=1.27 (s, 18H); 1.60 (s, 6H); 1.79 (s, 3H); 5.32 (s, 2H); 7.43 (s, 1H); 7.50 (s, 1H) ppm.

EXAMPLE 9

3-[(Aminooxy)methyl]-6,7-dihydroxy-2-quinoxalinecarboxylic acid, hydrochloride A suspension of the compound of Example 8 (4.1 g; 7.5 mmol) in 60 ml conc. HCl was heated at 80°–85° C. for 90 minutes. Over this period of time the starting material of Example 8 was dissolved to form finally a new precipitate. After cooling to 0° C. the precipitate was collected by suction, washed with few ml conc. HCl and dried in vacuo over P$_2$O$_5$; yield 1.9 g (88%) C$_{10}$H$_9$N$_3$O$_5$.1.6 HCl. 0.5 H$_2$O % C calc. 37.71%, found 38.64% % H calc. 3.67%, found 3.48% % N calc. 13.19%, found 12.80% % Cl calc. 17.81% found 17.70% IR(KBr): 1720 cm$^{-1}$; $^1$H-NMR (D$_2$O): δ=5.32 (s 2H); 6.53 (s, 1H); 6.63 (s, 1H) ppm.

EXAMPLE 10

[2R-[2α,3α(Z)]]-3-[[[[1-[2-(Formylamino)-4-thiazolyl]-2-[(2-methyl-4-oxo-1-sulfo-3-azetidinyl)amino]-2-oxoethylidene]amino]oxo]methyl]-6,7-dihydroxy-2-quinoxalinecarboxy acid, disodium salt The compound of Example 7 (9.6 g; 0.015 mol) was dissolved in water (80 ml) and the pH of the filtered solution was lowered to 2.0 by the addition of 2N HCl. Then the hydrochloride salt of Example 9 (1.44 g; 5.0 mmol) was added in small portions while the pH of the solution was corrected constantly to 2.0 by addition of 2N NaOH. Stirring at this pH (2.0) was continued for additional 4.5 hours, then the pH of the suspenion was adjusted to 5.5–6.0 by addition of 2N NaOH and the nearly clear solution was filtered and freeze-dried. The obtained powder was redissolved in water (75 ml), filtered again and passed through a column with Dowex 50 W×8.20–50 mesh (Na$^+$-form). Freeze-drying of the relevant fractions yielded 5.6 g of an orange, crude material which was chromatographed (MPLC) on XAD-2 resin eluting with water to remove inter alia recovered sodium salt of the starting material of Example 7. Fractions containing the title compound with an HI≧85% by HPLC (yield 15%) were rechromatographed on XAD-2 resin eluting with water to yield after freeze-drying an yellowish powder with an HI=95.1% by HPLC.

IR(KBr): 1755 cm$^{-1}$ $^1$H-NMR(DMSO-d$_6$): δ=1.14 (d, 3H; J=7 Hz), 4.00 (quin (ps), 1H; J=7 Hz; J'=6 Hz); 5.15 (dd, 1H J'=6 Hz; J"=9 Hz); 5.55 (d, 1H; J=14 Hz); 5.70 (d, 1H; J=14 Hz); 6.76 (s, 1H); 6.98 (s, 1H); 7.38 (s, 1H); 7.38 (s, 1H); 8.46 (s, 1H); 9.97 (d, 1H; J"=9 Hz) ppm.

EXAMPLE 11

[2R-[2α,3α(Z)]]-3-[[[[1-(2-Amino-4-thiazolyl)-2-[(2-methyl-4-oxo-1-sulfo-3-azetidinyl)amino]-2-oxoethylidene]amino]oxy]methyl]-6,7-dihydroxy-2-quinoxalinecarboxylic acid To a solution of 228 mg (0.36 mmol) of the compound of Example 10 (HI=95% by HPLC) in 90 ml water, 27 ml tetrahydrofuran were added and then the pH of the solution was lowered to pH=0.8–1.0 by the addition of 2N hydrochloric acid. The mixture was stirred at room temperature for 20 hours to deformylate ca. 90% of the starting material Example 10, (proven by HPLC). The precipitated yellowish zwitterion title compound was collected by suction, washed with water and purified by redissolving in 10 ml water at pH 5.5–6.0 (addition of 0.5N NaOH) and reprecipitation at pH 1.0 (addition of 2N HCl). After stirring for additional 30 minutes the precipitate was collected by suction, washed with few ml water and dried in vacuo over P$_2$O$_5$ to yield 90 mg title compound with an HI of 97%; mp >200° decomposes.

IR(KBr): 1740 cm$^{-1}$ $^1$H-NMR(DMSO-d$_6$): δ=1.02(d, 3H; J=7 Hz); 3.97 (quin (ps), 1H; J=7 Hz; J'=6 Hz); 5.06 (dd, 1H, J'=6 Hz, J"=8 Hz); 5.63 (d, 1H, J=14 Hz); 5.70 (d, 1H; J=14 Hz) 6.91 (s, 1H); 7.28 (s, 1H); 7.30 (s, 1H); 9.42 (d, 1H; J"=8 Hz) ppm.

EXAMPLE 12

(2S-trans)-3-[[[2-(Formylamino)-4-thiazolyl]-oxoacetyl]amino]-2-methyl-4-oxo-1-azetidine-sulfonic acid, tetrabutylammonium (1:1) salt To a suspension of (2S-trans)-3-[[[2-(Formylamino)-4-thiazolyl]-oxoacetyl]amino]-2-methyl-4-oxo-1-azetidine-sulfonic acid, monopotassium salt (10.0 g; 0.025 mol) in water (250 ml), tetrabutylammonium-hydrogensulfate (10.32 g; 0.030 mol) was added and the pH was adjusted to 5.5–6.0 by the addition of 2N KOH. The mixture was extracted three times with chloroform (100 ml, 70 ml, 70 ml) and the combined organic layers were washed with a few ml water, dried (MgSO$_4$) and evaporated in vacuo to leave a viscous foam which solidified by stirring with petroleum ether (bp 60°–80° C.); the solid was collected by suction and dried in vacuo over P$_2$O$_5$; mp=82° C. (sint), 120.5° C. dec; yield: 13.23 g (87%).

C$_{26}$H$_{45}$N$_5$O$_7$S$_2$% C calc. 51.72%, found 51.03% % H calc. 7.51%, found 7.51% % N calc. 11.60%, found 11.60% IR(KBr): 1770, 1670 cm$^{-1}$; $^1$H-NMR(DMSO-d$_6$): δ=0.91 (t, 12H); 1.43 (d, 3H); J=7 Hz); 1.10–1.80 (m, 16H); 3.00–3.30 (m, 8H); 3.82 (dq), 1H; J=7 Hz, J'=3 Hz); 4.46 (dd, 1H, J'=3 Hz, J"=8 Hz); 8.54 (s, 1H); 8.57 (s, 1H); 9.78 (d, 1H, J"=8 Hz); 12.68 (s, broad, 1H).

EXAMPLE 13

[2S-[2α,3β(Z)]]-3-[[[[1-[2-Formylamino]-4-thiazolyl]-2-[(2-methyl-4-oxo-1-sulfo-3-azetidinyl)amino]-2-oxoethyliene]amino]oxy]methyl]-6,7-dihydroxy-2-quinoxalinecarboxylic acid, disodium salt The compound of Example 12 (4.53 g; 7.5 mmol) was dissolved in water (40 ml) and the pH of the filtered solution was lowered to 2.0 by the addition of 2N HCl Then the hydrochloride salt of Example 9 (1.44 g; 5.0 mmol) was added in small portions while the pH of the solution was corrected constantly to 2.0 by addition of 2N NaOH. Stirring at this pH (2.0) was continued for additional 4.5 hours, then the pH of the suspension was adjusted to 5.5–6.0 by addition of 2N NaOH and the nearly clear solution was filtered and freeze-dried. To replace the tetrabutylammonium cation by the Na-cation the so obtained powder was redissolved in water (40 ml), filtered again and passed through a column with Dowex 50W×8, 20–50 mesh (Na+-form). Freeze-drying of the relevant fractions yielded 5.0 g of an orange, crude material which was chromatographed (MPLC) on XAD-2 resin eluting with water to remove recovered sodium salt of the starting material of Example 12.

Fractions containing the title compound with an HI≧88% by HPLC (yield 14%) were rechromatographed on XAD-2 resin eluting with water to yield after freeze-drying a yellowish powder with an HI=95.6% by HPLC: yield 140 mg (4.4%).

IR(KBr): 1760 cm$^{-1}$; $^1$H-NMR(DMSO-d$_6$-TFA) δ=1.39 (d, 3H; J=7 Hz), 3.77 (dq), 1H; J=7 Hz), 4.44 (d), 1H; J'=3 Hz); 5.60 (d, 1H; J=14 Hz); 5.68 (d, 1H; J=14 Hz); 7.32 (s, 1H); 7.33 (s, 1H); 7.38 (s, 1H); 8.46 (s, 1H) ppm.

EXAMPLE 14

[2S-[2α, 3β(Z)]]-3-[[[[1-(2-Amino-4-thiazolyl)-2-[(2-methyl-4-oxo-1-sulfo-3-azetidinyl)amino]-2-oxoethylidene]amino]oxy]methyl]-6,7-dihydroxy-2-quinoxalinecarboxylic acid To a solution of 120 mg (0.19 mmol) (HI=93–95% by HPLC) in water (45 ml) tetrahydrofuran (13.5 ml) was added and then the pH of the solution was lowered to pH=0.8–1.0 by the addition of 2N hydrochloric acid. The mixture was stirred at room temperature for 27 hours to deformylate ca. 90% of the starting material (proven by HPLC). The still clear solution was concentrated in vacuo to half of its volume and the pH was adjusted to 1.0 by the addition of 0.5N NaOH. After cooling to 5° C. the precipitated yellowish zwitterion title compound was collected by suction, washed with ice water and purified by redissolving in 7 ml water at pH 5 (addition of 0.5N NaOH) and reprecipitation at pH 1.0 (addition of 2N HCl). After stirring for additional 30 minutes at 10° C. the precipitate was collected by suction, washed with a few ml ice water and dried in vacuo over $P_2O_5$ to yield 70 mg (65%) title compound.

IR(KBr): 1760 cm$^{-1}$; M.P.=>178° C. decomposes $^1$H-NMR(DMSO-d$_6$): δ=1.37 (d, 3H; J=7 Hz); 3.72 (dq, 1H; J=7 Hz; J'=3 Hz); 4.42 (dd, 1H, J'=3 Hz, J''=8 Hz); 5.66 (s, 2H); 6.89 (s, 1H); 7.28 (s, 1H); 7.30 (s, 1H); 9.47 (d, 1H; J''=8 Hz ) ppm.

EXAMPLE 15

[2R-[2α,3α(Z)]]-3-[2-[[[1-(2-Amino-4-thiazolyl)-2-[(2-methyl-4-oxo-1-sulfo-3-azetidinyl)amino]-2-oxoethylidene]amino]oxy]ethyl]-6,7-dihydroxy-2-quinoxalinecarboxylic acid

EXAMPLE 15A 3-oxo-5-(phenylmethoxy)pentanoic acid, 1,1-dimethylethyl ester

Analogous to the procedure described by Brooks, D. W., Kellogg, R. P. and Cooper, C. S., *J. Org. Chem.* 52 192, (1987) t-butyl acetate (33 ml; 0.20 mol) and benzyl chloromethylether (50 ml; 0.22 mol) were reacted. Chromatographic purification on silica gel eluting with petroleum ether/ethyl acetate (5:1) afforded the title compound as a viscous oil still containing ca 10% (by NMR) of t-butyl acetoacetate. This material was used in the next step without any additional purification. Yield 3.41 g (61%).

IR(film): 1738, 1712 cm$^{-1}$; $^1$H-NMR(DMSO-d$_6$): δ=1.34 (s, 9H); 2.72 (t, 2H; J=7 Hz); 3.43 (s, 2H); 3.60 (t, 2H; J=7 Hz); 4.39 (s, 2H); 7.27 (s(ps), 5 H) ppm.

EXAMPLE 15B 2-(Hydroxyimino)-3-oxo-5-(phenylmethoxy)pentanoic acid, (1,1-dimethylethyl) ester With stirring and cooling (0° C.) a solution of sodium nitrite (1.5 g; 22 mmol) in water (5 ml) was dropped within 10 minutes into a solution of compound of Example 15A (5.56 g; 20 mmol) in acetic acid (3.0 g; 50 mmol) and stirring was continued at 0° C. for additional 10 minutes and at room temperature for 30 minutes. The reaction product was extracted with ether and the combined ether phases were washed with aqueous sodium-bicarbonate solution and brine. After drying (CaSO$_4$) the solvent was removed in vacuo to leave a residue (5.7 g) which solidified by treatment with petroleum ether (bp 60°–70° C.). Yield: 3.65 g (59.5%) mp: 98°–100° C. (mp: 100°–101° C. after recrystallization from ether-petroleum ether).

IR(KBr):1730, 1679 cm$^1$; $^1$H-NMR(DMSO-d$_6$): δ=1.46(s, 9H); 3.02(t, 2H; J=7 Hz); 3.70(t, 2H; J=7 Hz); 4.45(s, 2H); 7.31 (s(ps), 5H); 13.10(s(broad), 1H) ppm.

EXAMPLE 15C 2-3-dioxo-3-(phenylmethoxy)butanoic acid 1,1-dimethylethyl ester, hydrate Anhydrous sodium sulfate (10.0 g) was added to a solution of the compound of Example 15B (28.8 g; 94 mmol) in chloroform (250 ml) at −25° C. followed by a solution of dinitrogen tetroxide (4.4 g; 48.0 mmol) in dry chloroform (60 ml). After stirring at −25° C. for 5 hours the mixture was allowed to warm to room temperature within 4 days. After filtration (Na$_2$SO$_4$) and removal of the solvent in vacuo the residual oil (30 g) was dissolved in ethyl acetate, washed with aqueous NaHCO$_3$ solution (10%) and brine. Drying (CaSO$_4$) and removal of the solvent on a rotary evaporator yielded an oil, which was used in the next step without any further purification: yield: 27.5 g (94%).

EXAMPLE 15D 2,2-Dimethyl-7-[2-(phenylmethoxy)ethyl]-1,3-dioxolo]4,5g]quinoxaline-6-carboxylic acid, 1,1-dimethylethyl ester The freshly prepared, crude compound, 5,6-diamino-2,2-dimethyl)-1,3-benzodioxole, (16.4 g; 91 mmol) was taken up in a mixture of water (180 ml) and tetrahydrofuran (90 ml) and then the crude compound of Example 15C (27.5 g; ca 90 mmol) was added with stirring. The mixture was refluxed for 60 minutes at 80°–85° C. and then evaporated in vacuo to leave a residue which was partitioned between ethyl acetate (350 ml) and water (150 ml). After extraction of the aqueous phase with ethyl acetate the combined organic phases were washed with brine and dried (Na$_2$SO$_4$). Removal of the solvent in vacuo gave an oily residue which was purified by chromatography on silica gel eluting with ethyl acetate/petroleum ether (bp 60°–70° C.). Yield: 20.2 g (51%).

IR(film): 1735, 1720 (sh) cm$^{-1}$; $^1$H-NMR (DMSO-d$_6$) δ=1.56(s, 9H); 1.77 (s, 6H); 3.31 (t, 2H; J=7 Hz); 3.81 (t, 2H)7; J=7 Hz); 4.44 (s, 2H); 7.23(s(ps), 5H); 7.30(s, 1H); 7.38 (s, 1H) ppm.

EXAMPLE 15E 7-(2-Hydroxyethyl)-2,2-dimethyl-1,3-dioxolo-[4,5g]quinoxaline-6-carboxylic acid, (1,1-dimethylethyl) ester.

The compound of Example 15D (10.5 g; 24.0 mmol) was dissolved in dimethylformamide (200 ml) and hydrogenated for 15 minutes in the presence of palladium (10%) on carbon (3.0 g). The catalyst was removed by filtration and the solvent was distilled off in vacuo. The residue was dissolved in ethyl acetate, washed with water and brine, dried (Na$_2$SO$_4$) and evaporated in vacuo to leave a residual oil (8.1 g) which was chromatographically purified on silica gel eluting with ethyl acetate/petroleum ether (45:55). Yield 6.2 g (75%); mp 88°–90° C. (90°–92° from petroleum ether). $C_{18}H_{22}N_2O_5$

| Elemental analysis (%) | C₁₈H₂₂N₂O₅ Calc. | Found |
|---|---|---|
| C | 62.41 | 62.27 |
| H | 6.40 | 6.37 |
| N | 8.09 | 8.19 |

IR(KBr): 1735 cm⁻¹; ¹H-NMR(DMSO-d₆): δ=1.60(s, 9H); 1.79 (s, 6H); 3.18 (t, 2H; J=7 Hz); 3.78(q(ps), 2H; J=7 Hz; J'=7 Hz); 4.76(t, 1H; J'=7 Hz); 7.33 (s, 1H); 7.40(s, 1H) ppm.

EXAMPLE 15F

7-[2-[[Bis[(1,1-dimethylethoxy)carbonyl]amino]oxy]ethyl-2,2-dimethyl-1,3-dioxolo]4,5g]-quinoxaline-6-carboxylic acid, 1,1-dimethylethyl ester A solution of diethyl azodicarboxylate (5.0 g; 28.6 mmol) in dry tetrahydrofuran (40 ml) was dropped at room temperature into a mixture of the compound of Example 15E (9.9 g; 28.6 mmol), triphenylphosphine (7.5 g; 28.6 mmol) and Hydroxyimidodicarbonic acid, bis(1,1-dimethylethyl) ester (6.1 g; 26 mmol) in dry tetrahydrofuran (100 ml) and stirring was continued for 5.5 hours at room temperature. The solvent was removed in vacuo and the residue was purified by chromatography on silica gel eluting with petroleum ether/ethyl acetate (gradient 20-30%); first fractions contained the corresponding vinyl-compound (dehydrated starting material; yield 4.5 g; 53%), late fractions the desired titled compound; yield: 4.8 g (33%); viscous oil.

IR (film): 1785, 1750, 1720 cm⁻¹; ¹H-NMR(DMSO-d₆: δ=1.35 (s, 18 H); 1.59 (s, 9H); 1.78 (s, 6H); 3.37 (t, 2H); 7.33 (s, 1H); 7.41 (s, 1H) ppm.

EXAMPLE 15G

3-[2-(Aminooxy)ethyl]-6,7-dihydroxy-2-quinoxaline-2-carboxylic acid .HCl

In a simple vacuum distillation apparatus a mixture of the compound of Example 15F (1.8 g; 3.3 mmol) and conc. HCl (70 ml) was heated at 85°-90° C. and ca 700 mbar to distill off the generated acetone. After 90 minutes, the mixture was evaporated in vacuo to leave a yellow solid (1.0 g) which still contained ca 20% of the corresponding acetone-oxime of the title compound. Rehydrolysis of this solid with conc. HCl (40 ml) using the same conditions (85°-90° C.; 700 mbar) afforded after cooling (0° C.) a precipitate, which was collected by suction, washed with few ml conc. HCl and dried in vacuo over P₂O₅: yield 0.4 g (40%); mp:>300° C.; HI=96% (by HPLC).

IR(KBr): 1750 cm⁻¹; ¹H-NMR(DMSO-d₆/trifluoroacetic acid 1:1): δ=3.56 (t, 2H); 4.42 (t, 2H); 7.32 (s, 1H); 7.38 (s, 1H) ppm.

EXAMPLE 15H

[2R-[2α,3α(Z)]]-3-[2-[[[1-[2-(Formylamino)-4-thiazolyl]-2-[(2-methyl-4-oxo-1-sulfo-3-azetidinyl)amino]-2-oxoethylidene]amino]oxy]ethyl]-6,7-dihydroxy-2-quinoxalinecarboxylic acid, tetrabutylammonium (1:2) salt The tetrabutylammonium salt of Example 7 (0.78 g; 1.30 mmol) was dissolved in water (35 ml) and the pH of the filtered solution was lowered to 1.9 by the addition of tetrabutylammonium hydrogen sulfate (0.21 g). Then the hydrochloride salt of Example 15G (0.39 g; 1.30 mmol) was added in small portions while the pH of the solution was corrected constantly to 2.0 by addition of a solution of tetrabutylammonium hydroxide in water (20%). Stirring at this pH (2.0) was continued for additional 4.0 hours, then the pH of the suspension was adjusted to 5.8 by addition of tetrabutylammonium hydroxide and the clear solution was freeze-dried to yield 2.5 g of an orange, crude material which was chromatographed (MPLC) on XAD-2 resin eluting with water-acetonitrile (15%).

The E-isomer was isolated from the first fractions (yield: 240 mg, 17%) whereas late fractions contained the pure isomer of the title compound yield: 355 mg (25%); mp: 110° sint, 134°-136° C.; HI=97.7% by HPLC.

IR(KBr): 1765 cm⁻¹, 200 MHz-¹H-NMR(DMSO-d₆-TFA): δ=0.90(t, 24H); 1.15-1.42 (m, 16H) overlapped by 1.28 (d, 3H, J=7 Hz); 1.42-1.75 (m, 16H); 3.0-3.3 (m, 18H); 3.57 (t, 2H; J''=7 Hz); 4.00 (quin(ps), 1H, J=7 Hz, J'=6 Hz); 4.55 (t, 2H, J'''=7 Hz); 5.09 (d, 1H, J'=6 Hz); 7.26 (s, 1H); 7.32 (s, 1H); 7.35 (s, 1H); 8.48 (s, 1H) ppm.

EXAMPLE 15I

[2R-[2α,3α(Z)]]-3-[2-[[[1-(2-Amino-4-thiazolyl)-2-[(2-methyl-4-oxo-1-sulfo-3-azetidinyl)amino]-2-oxoethylidene]amino]oxo]ethyl]-6,7-dihydroxy-2-quinoxaline-carboxylic acid To a solution of the tetrabutylammonium salt of Example 15H (317 rag, 0.29 mmol) purity=98% by HPLC) in water (72 ml) was added tetrahydrofuran (22 ml) and then the pH of the solution was lowered to a pH of 0.6 by the addition of 2N hydrochloride acid (15 ml). The mixture was stirred at room temperature for 18 hours and the precipitated yellowish zwitterion title compound was collected by suction, washed with a few ml ice-water and dried in vacuo over P₂O₅: yield: 105 mg (62.5%); mp:>300° C.; purity:98.6% (by HPLC). C₂₀H₁₉N₇O₁₀S₂.2.5 H₂O

| Elemental analysis | C₂₀H₁₉N₇O₁₀S₂.2.5 H₂O Calc. | Found |
|---|---|---|
| C | 38.33 | 38.28 |
| H | 3.86 | 3.95 |
| N | 15.65 | 15.40 |

IR(KBr): 1740 cm⁻¹; ¹H-NMR(DMSO-d₆/trifluoroacetic acid): δ=1.07(d, 3H, J=7 Hz); 3.65 (t, 2H); 3.98 (quintett(ps), 1H), J=7 Hz, J''=6 Hz); 4.68 (t, 2H); 5.02 (d, 1H, J'6 Hz); 6.89 (s, 1H); 7.28 (s, 1H); 7.40 (s, 1H); ppm.

EXAMPLE 16

Alternate Method for Preparation of [2R-[2α3α(Z)]]-3-[2-[[[1-(2-Amino-4-thiazolyl)-2-[(2-methyl-4-oxo-1-sulfo-3-azetidinyl)amino]-2-oxoethylidene]amino]oxy]ethyl]-6,7-dihydroxy-2-quinxoalinecarboxylic acid

EXAMPLE 16A (2R-cis)-3-[[[2-Formylamino)-4-thiazolyl]oxoacetyl]amino]-2-methyl-4-oxo-1-azetidine-sulfonic acid monopotassium salt 1,8-Diazobicyclo[5.4.0]undec-7-ene (DBU) (16.5 ml; 0.11 mol) was dropped into a suspension of the zwitterion (2R-cis)-3-Amino-2-methyl-4-oxo-1-azetidine-sulfonic acid, inner salt (18.02 g; 0.10 mol) in dry dichloromethane (180 ml) at 10° C. and stirring was continued at this temperature for an additional hour. Then the solution was cooled to −30° C. (solution A). Formylaminothiazolylglyoxylic acid (22.22 g; 0.111 mol) was suspended in dry dichloromethane (360 ml) and then dissolved by addition of triethylamine (17.0 ml; 0.122 mol). After being stirred for 1 additional hour insoluble material was filtered off and the filtrate was cooled to −30° C. (solution B).

Into solution B was added dropwise at −30° C. pyridine (0.62 ml) followed by trimethylacetyl chloride (13.38 g; 0.111 mol) and then by solution A. The mixture was stirred at −25° to −30° C. for 1 hour and then allowed to come to ambient temperature. After evaporation in vacuo the residue was taken up in ethanol (600 ml) and treated dropwise with a solution of potassium acetate (28 g; 0.285 mol) in ethanol (180 ml). After being stirred for 1 hour the precipitate was collected by suction, washed with ethanol, dried in vacuo and purified by recrystallization from hot water (270 ml). Yield 28.4 g (70%); mp >230° C.

IR(KBr) 1755, 1670 cm$^{-1}$; $^1$H-NMR(DMSO-d$_6$): δ=1.22 (d, 3H); J=7 Hz); 4.07(quin(ps), 1H; J=7 Hz; J'=6 Hz); 5.11 (dd, 1H; J'=6 Hz; J''=8.5 Hz); 8.45 (s, 1H); 8.56 (s, 1H); 9.40 (d, 1H; J''=8.5 Hz); 12.70 (s, 1H) ppm.

EXAMPLE 16B (2R-cis)-3-[[(2-Amino-4-thiazolyl)oxoacetyl]amino]-methyl-4-oxo-1-azetidine-sulfonic acid The compound from Example 16A (20 g, 55.2 mmol) was suspended in 270 ml water. The pH was brought to 0.5 with 3N hydrochloric acid and the resulting solution was stirred for two days at room temperature. On taking a sample for tlc analysis, the title compound precipitated. It was filtered off with suction, washed with water and dried in vacuo. Yield 12.6 g (68.4%) m.p. >300° C.

IR(KBr): 1710, 1760 cm$^{-1}$ (CO). $^1$H-NMR(DMSO-d$_6$): δ=1.20 (d, 3H), 4.03 (dq, 1H), 5.02 (dd, 1H), 8.19 (s, 1H), 8.35 (s, broad, NH$_2$, SO$_3$H and water), 9.70 (d, 1H); ppm.

EXAMPLE 16C

[2R-[2α,3α(Z)]]-3-[2-[[[1-(2-Amino-4-thiazolyl)-2-[(2-methyl-4-oxo-1-sulfo-3-azetidinyl)amino]-2-oxoethylidene]amino]oxy]ethyl]-6,7-dihydroxy-2-quinoxaine-carboxylic acid The compound from Example 16B (0.33 g, 1.0 mmol) was suspended in water (15 ml) and the pH was adjusted to 5.5-6.0 by addition of a solution of tetrabutylammonium hydroxide in water (20%) to obtain a clear solution. The pH of this solution was lowered to 2.0 by the addition of tetrabutylammonium hydrogen sulfate (0.14 g). Then the hydrochloride salt of 3-[2-Aminooxy)ethyl]-6,7-dihydroxy-2-quinoxaline-2-carboxylic acid (0.5 g; ca 1.0 mmol; Hl by HPLC: 64%) (Example 15G) was added in small portions while the solution was corrected constantly to 2.0 by addition of a solution of tetrabutylammonium hydroxide in water (20%). Stirring at this pH (2.0) was continued for additional 4.5 hours, then the pH of the suspension was adjusted to 5.8 by addition of tetrabutylammonium hydroxide and the solution was freeze-dried to yield 1.7 g of an orange, crude material which was chromatographed (MPLC) on XAD-2 resin eluting with water-acetonitrile (gradient 10-15%). Freeze-drying of the appropriate fractions yielded 0.18 g (17%) of the di-tetrabutylammoniumsalt [2R-[2α,3α(Z)]]-3-[2-(Formylamino)-4-thiazolyl]-2-[(2-methyl-4-oxo-1-sulfo-3-azetidinyl)amino]-2-oxoethylidene]amino]oxy]-ethyl]-6,7-dihydroxy-2-quinoxalinecarboxylic acid, from which the title compound was obtained by dissolving in water (15 ml) and precipitation at pH 2.0 (addition of 2N HCl). Yield: 50 mg (54%); mp: >dec. 198° C.

EXAMPLE 17

[2R-[2α,3α(Z)]]-3-[3-[[[1-(2-Amino-4-thiazolyl-2-[(2-methyl-4-oxo-1-sulfo-3-azetidinyl)amino]-2-oxoethylidene]amino]oxy]propyl]-6,7-dihydroxy-2-quinoxalinecarboxylic acid

EXAMPLE 17A

7-[(Dimethoxyphosphinyl)methyl]-2,2-dimethyl-1,3-dioxolo[4,5-g]quinoxaline-6-carboxylic acid, 1,1-dimethylethyl ester A mixture of the compound of Example 3 (3.95 g; 10.0 mmol) and trimethyl phosphite (3.5 ml; 30.0 mmol) was heated in an oil bath at 140° C. for 30 minutes and the volatile components were distilled off during this period. On cooling, the residue was taken up in petroleum ether and evaporated in vacuo to leave a viscous oil (5 g), which was purified chromatographically on silica gel eluting with ethyl acetate. Evaporation of the appropriate fractions in vacuo afforded a colorless oil, which solidified by stirring with a few ml petroleum ether. Yield 2.77 g (65%); mp=86.3°-87.9° C. (from petroleum ether). $C_{19}H_{25}N_2O_7P$

|   | $C_{19}H_{25}N_2O_7P$ | |
|---|---|---|
|   | Calc. (%) | Found (%) |
| C | 53.77 | 53.45 |
| H | 5.94 | 6.08 |
| N | 6.60 | 6.92 |

IR(KBr): 1720 cm$^{-1}$; 200 MHz-$^1$H-NMR(DMSO-d$_6$): δ=1.57 (s, 9H); 1.75 (s, 6H); 3.58 (d, 6H, J($^{31}$P-$^1$H)=11.0 Hz); 3.92 (d, 2H, J($^{31}$P-$^1$H)=22.4 Hz); 7.36 (s, 1H); 7.42 (s, 1H) ppm.

EXAMPLE 17B

7-[3-Acetyloxy)-1-propenyl]-2,2-dimethyl-1,3-dioxolo[4,5g]quinoxaline-6-carboxylic acid, 1,1-dimethylethyl ester A solution (2.5 M) of n-butyllithium (12 ml; 30.1 mmol) was treated dropwise with a solution of diisopropylamine (4.2 ml; 30.0 mmol) in dry tetrahydrofuran (40 ml) with stirring at 0° C. The mixture was held at 0° C. for 30 minutes and then cooled to −30° C. A solution of the phosphonate of Example 17a (12.7 g; 30.0 mmol) in dry tetrahydrofuran (80 ml) was added dropwise and after being stirred at −30° C. for another 30 minutes, a solution of 2-acetoxy-acetaldehyde (3.06 g; 30.0 mmol) in dry tetrahydrofuran (60 ml) was added slowly. The mixture was allowed to come to ambient temperature and stirring was continued for an additional 2 hours at this temperature. The solvent was removed on a rotary evaporator and the residue was taken up in ethyl acetate and water and the pH was adjusted to 3 by the addition of 2N HCl. The organic layer was separated, washed with brine, and dried (MgSO$_4$). After removal of the solvent in vacuo the oily residue (14.9 g) was purified by chromatography on silica gel eluting with ethyl acetate petroleum ether (1.3) to give the title compound as a mixture of stereoisomers. Yield: 7.2 g (60%).

EXAMPLE 17C 7-(3-Hydroxypropyl)-2,2-dimethyl-1,3-dioxolo[4,5g-]quinoxaline-6-carboxylic acid 1.1-dimethylethyl ester The mixture of isomers from Example 17B (3.82 g; 9.5 mmol) was dissolved in dry methanol (270 ml) and hydrogenated for 12 minutes (monitored by tlc) in the presence of palladium (10%) on carbon (2 g). After removal of the catalyst by filtration and evaporation of the filtrate in vacuo an oily residue was obtained (10.4 g) containing ca 70% (by NMR) of the desired 7-(3-Acetyloxy)propyl)-2,2-dimethyl-1,3-dioxolo[4,5g-]quinoxaline-6-carboxylic acid, 1,1-dimethylethyl ester and ca 30% (by NMR) of a propyl side product. This crude residue was used in the next step without any purification.

To a stirred solution of the so obtained residue (3.62 g) in methanol (100 ml) was added a solution of potassium hydroxide (1.51 g; 27 mmol) in water (7 ml) and stirring was continued at room temperature for 30 minutes. The solvent was removed on a rotary evaporator and the residue was taken up in ethyl acetate and water. The pH of the mixture was brought to 3 by addition of 2N HCl and then the mixture was extracted with ethyl acetate.

The combined organic layers were washed with brine, dried (MgSO4) and evaporated to leave a residue which was chromatographed on silica gel eluting with petroleum ether/ethyl acetate (3:1). The propyl-compund was eluted first (yield: 0.61 g; mp: 91.7°–93.1° C.) then the desired alcohol yield: 0.99 g (30%); mp: 97.6°–98.1° C. (from petroleum ether bp 60°–70° C.). Using only 1 equivalent potassium hydroxide the yield of the desired alcohol can be raised up to 70%. $C_{19}H_{24}N_2O_5$ (360.4)

| $C_{19}H_{24}N_2O_5$ (360.4) | | |
|---|---|---|
| Elemental analysis (%) | Calc. | Found |
| C | 63.32 | 63.04 |
| H | 6.71 | 6.74 |
| N | 7.77 | 7.85 |

IR(KBr): 1725 cm$^{-1}$; $^1$H-NMR(DMSO-d$_6$): δ=1.60 (s, 9H); 1.7–2.0 (m, 8H; overlapped by singulett δ=1.77); 3.02 (t, 2H); 3.48 (q(ps), 2 H); 4.57 (t, 1H); 7.32 (s, 1H); 7.37 (s, 1H) ppm.

EXAMPLE 17D

7-[3-[[Bis[(1,1-dimethylethoxy)carbonyl]amino]oxy]-propyl]-2,2-dimethyl-1,3-dioxolo[4,5g]-quinoxaline-6-carboxylic acid, 1,1-dimethylethyl ester A solution of diethyl azodicarboxylate (0.35 ml; 2.2 mmol) in dry tetrahydrofuran (3 ml) was dropped at room temperature to a mixture of the compound of Example 17D (0.80 g; 2.2 mmol), triphenylphosphine (0.58 g; 2.2 mmol) and Hydroxyimidodicarbonic acid, bis(1,1-dimethylethyl) ester (0.47g; 2.0 mmol) in dry tetrahydrofuran (13 ml) and stirring was continued for 4 to 5 hours at room temperature. The solvent was removed in vacuo and the residue was purified by chromatography on silica gel eluting with petroleum ether-/ethyl acetate (gradient 20–30%); yield: 0.55 g (48%); viscous oil.

IR (film): 1792, 1751, 1720 cm$^{-1}$; $^1$H-NMR(DMSO-d$_6$): δ=1.33 (s, 18H); 1.49 (s, 9H); 1.68 (s, 6H); 1.90 (m$_c$, 2H); 3.00 (t, 2H); 3.89 (t, 2H); 7.20(s, 1H); 7.29 (s, 1H) ppm.

EXAMPLE 17E

3-[3-(Aminooxy)propyl]-6,7-dihydroxy-2-quinoxalinecarboxylic acid, hydrochloride A mixture of the compound of Example 17D (0.50 g; 0.87 mmol) and conc. HCl (5 ml) was heated at 85°–90° C. for 90 minutes. After cooling to 0° C. the precipitate was collected by suction, washed with a few ml conc. HCl and dried in vacuo over P$_2$O$_5$; yield: 0.22 g (80%); mp: dec >170° C.; purity by HPLC: 93%.

IR(KBr): 1710 cm$^{-1}$; $^1$H-NMR(DMSO-d$_6$/trifluoroacetic acid 1:1): δ=2.0–2.35 (m, 2H); 3.43 (t, 2H); 4.14 (t, 2H); 7.51 (s, 1H); 7.56 (s, 1H) ppm.

EXAMPLE 17F

[2R-[2α,3α(Z)]]-3-[3-[[[1-[2-(Formylamino)-4-thiazolyl]-2-[(2-methyl-4-oxo-1-sulfo-3-azetidinyl)amino]-2-oxoethylidene]amino]oxy]propyl]-6,7-dihydroxy-2-quinoxalinecarboxylic acid, tetrabutylammonium (1:2) salt (2R-cis)-3-[[[2-(Formylamino)-4-thiazolyl]oxoacetyl]amino]-2-methyl-4-oxo-1-azetidinesulfonic acid, N,N,N-tributyl-1-butanammonium salt (Example 7) (0.38 g; 0.63 mmol) was dissolved in water (12.5 ml) and the pH of the filtered solution was lowered to 2.0 by the addition of 2N HCl. Then the hydrochloride salt of Example 17E (0.18 g; 0.57 mmol) was added in small portions while the pH of the solution was corrected constantly to 2.0 by addition of a solution of tetrabutylammonium hydroxide in water (40%). Stirring at this pH (2.0) was continued for an additional 4.0 hours, then the pH of the suspension was adjusted to 5.5–6.0 by addition of tetrabutylammonium hydroxide and the nearly clear solution was filtered and freeze-dried to yield 1.0 g of an orange, crude material which was chromatographed (MPLC) on XAD-2 resin eluting with water-acetonitrile (10–20% gradient). The E-isomer was isolated from the first fractions (yield: 70 mg, 11%) whereas late fractions contained the pure Z-isomer of the title compound yield: 230 mg (36%); Purity=97% by HPLC.

IR(KBr): 1765 cm$^{-1}$; 200 MHz-$^1$H-NMR (DMSO): δ=0.92 (t, 24H); 1.17–1.42 (m, 16H) overlapped by 1.28 (d, 3H, J=7 Hz); 1.42–1.65 (m, 16H); 2.05 (m, 2H); 2.93 (t, 2H), J=7 Hz); 3.05–3.25 (m, 16H); 3.98 (quin(ps), 1H, J=7 Hz, J=6 Hz); 4.13 (t, 2H, J=7 Hz); 5.05 (dd, 1H, J=6 Hz, J=9 Hz); 7.02 (s, 1H); 7.06 (s, 1H); 7.37 (s, 1H); 8.48 (s, 1H); 9.65 (d, 1H, J=9 Hz) ppm.

EXAMPLE 17G

[2R-[2α,3α(Z)]]-3-[3-[[[1-(2-Amino-4-thiazolyl-2-[(2-methyl-4-oxo-1-sulfo-3-azetidinyl)amino]-2-oxoethylidene]amino]oxy]propyl]-6,7-dihydroxy-2-quinoxalinecarboxylic acid To a solution of the tetrabutylammonium salt of Example 17F (220 mg, 0.20 mmol) (purity=98% by HPLC) in water (48 ml) was added tetrahydrofuran (14.5 ml) and then the pH of the solution was lowered to 0.6 by the addition of 2N hydrochloride acid (10 ml). The mixture was stirred at room temperature for 72 hours and the precipitated yellowish zwitterion of the compound was collected by suction, washed with a few ml ice-water and dried in vacuo over P$_2$O$_5$; yield 80 mg (67%); M.P. dec. >203° C.; purity of 97.0% by HPLC. IR(KBr): 1740 cm$^{-1}$; $^1$H-NMR(DMSO-d$_6$-trifluoroacetic acid): δ=1.22 ( d, 3H, J=7 Hz); 2.17 (quintett (ps), 2H); 3.21 (t, 2H); 4.04 (quintett (ps), 1H, J=7 Hz, J″=6 Hz); 4.28 (t, 2H); 5.08 (d, 1H, J′=6 Hz); 6.97 (s, 1H); 7.26(s, 1H); 7.32 (s, 1H); ppm.

EXAMPLE 18

[2R-[2α,3α(Z)]]-3-[4-[[[1-(2-Amino-4-thiazolyl)-2-[(2-methyl-4-oxo-1-sulfo-3-azetidinyl)amino]-2-oxoethylidene]amino]oxy]butyl]-6,7-dihydroxy-2-quinoxalinecarboxylic acid

EXAMPLE 18A (E)-7-[4-(Acetyloxy)-1-butenyl]-2,2-dimethyl-1,3-dioxolo[4,5g]-quinoxaline-6-carboxylic acid, 1,1-dimethylethyl ester A solution (2.5M) of n-butyllithium (12 ml; 30.0 mmol) in hexane was treated dropwise with a solution of diisopropylamine (4.2 ml; 30.0 mmol) in dry tetrahydrofuran (50 ml) with stirring at −5° C. The mixture was held at 0° C. for 30 minutes, and then cooled to −30° C. A solution of the phosphonate of Example 15A was added dropwise and after being stirred at −30° C. for a further 30 minutes a solution of 3-Acetyloxypropanal prepared accordingly to a literature procedure: Hofstraat, R. G., Lange, J., Scheeren, H. W. and Nivard, R. J. F., *J. Chem. Soc. Perkin Trans* 1, 1988, 2315, (3.48 g; 30.0 mmol) in dry tetrahydrofuran (70 ml) was added slowly. The mixture was allowed to come to ambient temperature and stirring was continued for an additional 2 hours at this temperature. The solvent was removed on a rotary evaporator and the residue was taken up in ethyl acetate and water and the pH was adjusted to 3 by the addition of 2N HCl. The organic layer was separated, washed with brine, and dried (MgSO$_4$). After removal of the solvent in vacuo the oily residue (15.9 g) was purified by chromatography on silica gel eluting with ethyl acetate/petroleum ether (1:3) to give the title compound as a mixture of stereoisomers (E/Z). Yield: 6.5 g (52.6%).

Stirring off the mixture of stereoisomers (E/Z) with petroleum ether afforded the pure crystalline E-isomer, yield: 4.02 g (34%); mp: 90.7°–91.2° C. C$_{22}$H$_{26}$N$_2$O$_6$ (414.5)

| Elemental analysis (%) | C$_{22}$H$_{26}$N$_2$O$_6$(414.5) Calc. | Found |
|---|---|---|
| C | 63.76 | 63.11 |
| H | 6.32 | 6.39 |
| N | 6.76 | 6.71 |

IR(KBr): 1735, 1722 cm$^{-1}$; $^1$H-NMR(DMSO-d$_6$): δ=1.60 (s, 9H); 1.78 (s, 6H); 2.01 (s, 3H); 2.62 (q, 2H; J=6 Hz, J′=6 Hz); 4.19 (t, 2H, J=6 Hz); 6.82 (d, 1H, J″=16 Hz); 7.03 (dd, 1H, J′=6 Hz; J″=16 Hz); 7.30 (s, 1H); 7.38 (s, 1H) ppm.

EXAMPLE 18B

7-[4-Acetyloxy)]butyl]-2,2-dimethyl-1,3-dioxolo[4,5g-]quinoxaline-6-carboxylic acid, 1,1-dimethylethyl ester The E-isomer from Example 18A (3.60 g; 8.7 mmol) was dissolved in dry methanol (70 ml) and hydrogenated for 4 minutes (monitored by tlc) in the presence of palladium (10%) on carbon (0.5 g). After removal of the catalyst by filtration and evaporation of the filtrate in vacuo an oily residue was obtained containing the acetate and a trace of a butyl side product. This crude residue was used in the next step without any purification. Yield 3.58 g (99%).

EXAMPLE 18C 7-(4-Hydroxybutyl)-2,2-dimethyl-1,3-dioxolo[4,5g-]quinoxaline-6-carboxylic acid, 1,1-dimethylethyl ester To a stirred solution of the so obtained residue of Example 18B (3.54 g; 8.5 mmol) in methanol (95 ml) was added a solution of potassium hydroxide (0.52 g; 9.35 mmol) in water (6.5 ml) and stirring was continued at room temperature for 25 minutes. The solvent was removed on a rotary evaporator and the residue was taken up in ethyl acetate and water. The pH of the mixture was brought to 3 by addtion of 2N HCl and then the mixture was extracted with ethyl acetate. The combined organic layers were washed with brine, dried (MgSO$_4$) and evaporated to leave a residue which was chromatographed on silica eluting with petroleum ether/ethyl (acetate (3:1). A trace of the butyl compound was eluated first then the desired alcohol, yield: 2.94 g (92.5%).

Alternate method for preparing the title compound of Example 18C

EXAMPLE 18D

7-Formyl-2,2-dimethyl-1,3-dioxolo]4,5g]quinoxaline-6-carboxylic acid, 1,1-dimethylethyl ester Under argon the bromide of Example 3 (3.95, 10.0 mmol) was added to a solution of silver tetrafluoroborate (2.14 g; 11.0 mmol) in dry dimethyl sulfoxide (100 ml) and the mixture was stirred overnight at room temperature. After the addition of N,N-diisopropylethylamine (2.6 ml; 15.0 mmol) stirring was continued at room temperature for 24 hours and then the mixture was poured in ice-water (500 ml). The solution was extracted twice with ethyl acetate and the combined organic layers were washed with brine, dried (MgSO$_4$) and evaporated in vacuo to leave a residue (3.5 g) which separated yellowish needles when treated with few ml ethyl acetate/toluene (1:3). Yield: 1.30g (39%); mp: sint. 193° C., 194°–195° C. dec.

Chromatography of the mother liquor on silica gel eluting with ethyl acetate/toluene (1:3) afforded an additional quantity of the desired title compound (0.65g) besides the corresponding alcohol. Overall yield of the aldehyde title compound 1.95 g (59%). C$_{17}$H$_{18}$N$_2$O$_5$

| | C$_{17}$H$_{18}$N$_2$O$_5$ | |
|---|---|---|
| | Calc. (%) | Found (%) |
| C | 61.81 | 61.80 |
| H | 5.49 | 5.54 |
| N | 8.48 | 8.50 |

IR(KBr): 1735, 1705 cm$^{-1}$; 100 MHz-$^1$H-NMR(DMSO-d$_6$): δ=1.61 (s, 9H); 1.84 (s, 6H); 7.60 (s, 1H); 7.62 (s, 1H); 10.15 (s, 1H) ppm.

EXAMPLE 18E 2.2-Dimethyl-7-[4-(phenylmethoxy)-1-butenyl]-1.3-dioxolo[4,5g]quinoxaline-carboxylic acid, 1,1-dimethylethyl ester To a stirred suspension of 3-(Benzyloxy)propyl)-propyl)-triphenylphosphonium bromide prepared accordingly to the literature procedure: F. E. Ziegler, I. K. Scott, K. P. Uttam and W. Tein-Fu, *J. Amer. Chem. Soc.* 107, 2730 (1985) (10.3 g; 21.0 mmol) in dry tetrahydrofuran (500 ml) at 0° C. was added a 2.5M solution of n-butyllithium in hexane (8 ml; 20.0 mmol) over 30 minutes. Then a solution of the compound of Example 18D (6.9 g; 21.0 mmol) in dry tetrahydrofuran (230 ml) was added dropwise over 45 minutes at 0° C. After being stirred for 3 hours at room temperature the reaction mixture was filtered, the filtrate was evaporated in vacuo and the residue was taken up in ethyl acetate and water. The pH of the mixture was brought to 3 by addition of 2N HCl and then the mixture was extracted with ethyl acetate. The combined organic layers were washed with brine, dried ($Na_2SO_4$) and the solvent was removed on a rotary evaporator. The residue was chromatographed on silica gel eluting with ethyl acetate/toluene (1:3) to yield the desired olefin title compound as a mixture of stereoisomers (E/Z); yield: 6.28 g (68%); oil.

EXAMPLE 18F 7-(4-Hydroxybutyl)-2,2-dimethyl-1,3-dioxolo[4,5g-]quinoxaline-6-carboxylic acid, 1,1-dimethylethyl ester The olefin of Example 18E (mixture of stereoisomers) (3.01 g; 6.5 mmol) was dissolved in dry methanol (40 ml) and hydrogenated for 15 minutes (monitored by tlc) in the presence of palladium (10%) on carbon (0.5 g). After removal of the catalyst by filtration and evaporation of the filtrate in vacuo an oily residue of the still benzyl protected title compound was obtained which was used in the next step without any further purification Yield: 2.6 g (87%).

The crude benzyl-compound of above (2.53 g; 5.4 mmol) was dissolved in dry dimethyl formamide (30 ml) and then hydrogenated for 4 minutes in the presence of palladium (10%) on carbon (0.4 g). After the usual work-up the residue was chromatographed on silica gel eluting with petroleum ether/ethyl acetate (gradient) to afford recovered benzyl compound and the desired title compound. Rehydrogenation of the recovered benzyl-compound afforded after chromatographic purification the desired alcohol in an overall yield of 81% mp: 80.5°–81.5° C. (from ether/petroleum ether). $C_{20}H_{26}N_2O_5$ (374.4)

| $C_{20}H_{26}N_2O_5$ (374.4) | | |
|---|---|---|
| Elemental analysis (%) | Calc. | Found |
| C | 64.15 | 64.04 |
| H | 7.00 | 6.99 |
| N | 7.48 | 7.48 |

IR(KBr): 3350 cm$^{-1}$ (OH); 1727 cm$^{-1}$ (CO); $^1$H-NMR(DMSO-d$_6$): δ=1.3–1.9 (m, 4H; overlapped by 1.58 (s, 9H) and 1.76 (s, 6H); 2.98 (t, 2H; J=7 Hz); 3.40 (q(ps), 2H; J'=7 Hz); 4.40 (t, 1H; J''=7 Hz); 7.32 (s, 1H); 7.38 (s, 1H) ppm.

EXAMPLE 18G

7-[4-[[Bis[(1-dimethylethoxy)carbonyl]amino]oxy]-butyl]-2,2-dimethyl-1,3-dioxolo-[4,5g]quinoxaline-6-carboxylic acid, 1,1-dimethylethyl ester A solution of diethyl azodicarboxylate (1.62 ml; 10.3 mmol) in dry tetrahydrofuran (15 ml) was dropped at room temperature to a mixture of the compound of Example 18C or 18F (3.85 g; 10.3 mmol), triphenylphosphine (2.70 g; 10.3 mmol) and the title compound of Example 6 (2.19 g; 9.4 mmol) in dry tetrahydrofuran (70 ml) and stirring was continued for 3.5 hours at room temperature. The solvent was removed in vacuo and the residue was purified by chromatography on silica gel eluting with petroleum ether/ethyl acetate (gradient 20–30%); yield 4.32 g (71%), viscous oil.

IR (film): 1792, 1751, 1720 cm$^{-1}$; $^1$H-NMR(DMSO-d$_6$): δ=1.43 (s, 18H); 1.50–1.95 (m, 4H) overlapped by 1.49 (s, 9H) and 1.76 (s, 6H)) 3.01 (t, 2H); 3.87 (t, 2H); 7.31 (s, 1H); 7.39 (s, 1H) ppm.

EXAMPLE 18H

3-[4-(Aminooxy)butyl]6,7-dihydroxy-2-quinoxaline-2-carboxylic acid, hydrochloride In a simple vacuum distillation apparatus a mixture of the compound of Example 18G (2.68 g; 4.54 mmol) and conc. HCl (100 ml) was heated at 85°–90° C. and ca 700 mbar to distill off the generated acetone. After 2 hours the mixture was evaporated in vacuo to leave a yellow solid which was dissolved in few ml water and then freeze dried (1.78 g; purity=88.2% by HPLC). Rehydrolysis of this material with conc. HCl (70 ml) using similar conditions (80°–85°; 600 mbar) did not improve the purity of the desired compound. Yield: 1.58 g (quant.); purity=76.7 % (by HPLC). This material was used in the next step without any additional purification.

IR(KBr): 1750 cm$^{-1}$; $^1$H-NMR(DMSO-d$_6$/TFA 1:1): δ=1.7(m$_c$, 4H); 3.35(m$_c$, 2H); 4.05(m$_c$, 2H); 6.96 (s, 1H); 7.56(s, 1H) ppm.

EXAMPLE 18I

[2R-[2α,3α(Z)]]-3-[4-[[[1-[2-(Formylamino)-4-thiazolyl]-2-[(2-methyl-4-oxo-1-sulfo-3-azetidinyl-)amino]-2-oxoethylidene]]amino]oxy]butyl]-6,7-dihydroxy-2-quinoxalinecarboxylic acids, tetrabutylammonium (1:2) salt (2R-cis)-3-[[[2-(Formylamino)-4-thiazolyl]oxoacetyl]amino]-2-methyl-4-oxo-1-azetidinesulfonic acid, N,N,N-tributyl-1-butanamminium salt (Example 7) (1.21 g; 2.0 mmol) was dissolved in water (40 ml) and the pH of the filtered solution was lowered to 2.0 by the addition of tetrabutylammonium hydrogen sulfate (0.17 g). Then the hydrochloride salt of Example 18H (0.82 g; ca 2.0 mmol; purity by HPLC: 77%) was added in small portions while the pH of the solution was corrected constantly to 2.0 by addition of a solution of tetrabutylammonium hydroxide (TBA-OH) water (20%). Stirring at this pH (2.0) was continued for an additional 3.0 hours, then the pH of the suspension was adjusted to 5.8 by addition of tetrabutylammonium hydroxide and the solution was freeze-dried to yield 4.66 g of an orange, crude material which was chromatographed (MPLC) on XAD-2 resin eluting with water-acetonitrile (15%). Freeze-drying of the appropriate fractions yielded 0.43 g (19%) of a material with a purity (by HPLC) of 77–86% and 0.51 g (22.8%) of an additional crop with a purity by HPLC of 95.4–97.4%; overall yield: ca 37%; mp: 97° sint, dec. >100° C.

IR(KBr): 1762 cm$^{-1}$; 200 MHz-$^1$H-NMR(DMSO-d$_6$): δ=0.90 (t, 24 H); 1.10–1.40 (m, 16H) overlapped by 1.28 (d, 3H, J=7 Hz); 1.40–1.85 (m, 20H); 2.88 (t, 2H); J''=7 Hz); 3.25 (m, 16H); 3.97 (quin(ps), 1H, J=7 Hz, J'=6 Hz); 4.27 (t, 2H, J''=7 Hz); 5.06 (dd, 1H, J'=6 Hz; J'''=9 Hz); 7.01 (s, 1H); 7.15 (s, 1H); 7.32 (s, 1H); 8.48 (s, 1H); 9.46 (d, 1H; J'''=9 Hz) ppm.

EXAMPLE 18J

[2R-[2α,3α(Z)]]-3-[4-[[[1-(2-Amino-4-thiazolyl)-2-[(2-methyl-4-oxo-1-sulfo-3-azetidinyl)amino-[-2-oxoethylidene]amino]oxy]butyl]-6,7-dihydroxy-2-quinoxalinecarboxylic acid To a solution of the tetrabutylammonium salt of Example 18I (336 mg, 0.3 mmol) purity=97.4% by HPLC) in water (75 ml) was added tetrahydrofuran (25 ml) and then the pH of the solution was lowered to 0.6 by the addition of 2N hydrochloride acid (16 ml). The mixture was stirred at room temperature for 70 hours and the precipitated yellowish zwitterion title compound was collected by suction, washed with few ml ice-water and dried in vacuo over $P_2O_5$. Yield 160 mg (87.4%); mp: dec >217° C.; purity 98.8% (by HPLC). $C_{22}H_{23}N_7O_{10}S_2.2.6\ H_2O$

| $C_{22}H_{23}N_7O_{10}S_2.2.6\ H_2O$ | | |
|---|---|---|
| | Calc. | Found |
| C | 40.25 | 40.01 |
| H | 4.33 | 4.28 |
| N | 14.94 | 15.00 | p IR(KBr): 1745 cm$^{-1}$; $^1$H-NMR(DMSO-d$_6$-TFA): δ=1.18 (d, 3H, J=7 Hz); 1.80 (m$_c$, 4H); 3.30 (t, 2H); 4.05 (quintett(ps), 1H, J=7 Hz, J''=6 Hz); 4.20 (, 2H); 5.07 (d, 1H, J=6 Hz); 6.89 (s, 1H); 7.40 (s, 1H); 7.48 (s, 1H) ppm.

EXAMPLE 19

Alternate Preparation of [2R-[2α,3α(Z)]]-3-[4-[[[1-(2-Amino-4-thiazoly)-2)-2-[(2-methyl-4-oxo-1-sulfo-3-azetidinyl)amino]-2-oxoethylidene]amino]oxy]butyl]-6,7-dihydroxy-2-quinoxalinecarboxylic acid The compound of Example 17B (2S-cis)-3-[[[(2-Amino-4-thiazolyl)-oxoacetyl]amino]-2-methyl-4-oxo-1-azetidine-sulfonic acid (0.50 g, 1.5 mmol) was suspended in water (30 ml) and the pH was adjusted to 5.5–6.0 by addition of a solution of tetrabutylammonium hydroxide in water (20%) to obtain a clear solution. The pH of this solution was lowered to 2.0 by the addition of tetrabutylammonium hydrogen sulfate (0.14 g). Then the hydrochloride of Example 18H 3-[4-(Aminooxy)butyl]-6,7-dihydroxy-2-quinoxaline-2-carboxylic acid, monohydrochloride (0.62 g; ca 1.5 mmol); purity by HPLC; 77%) was added in small portions while the pH of the soltuion was corrected constantly to 2.0 by addition of a solution of tertrabutylammonium hydroxide in water (20%). Stirring at this pH (2.0) was continued for additional 3.0 hours, then the pH of the suspension was adjusted to 5.8 by addition of tertrabutylammonium hydroxide and the solution was freeze-dried to yield 3.12 g of an orange, crude material which was chromatographed (MPLC) on XAD-2 resin eluting with water-acetonitrile (12%). Freeze-drying of the appropriate fractions yielded 0.11 g (6.7%) of the di-TBA-salt from which the title compound was obtained by dissolving in water (10 ml) and precipitation at pH 2.0 (addition of 2N HCl). Yield: 30 mg (4%);mp: dec. 198° C.

EXAMPLE 20

Alternate Preparation of [2R-[2α,3α(Z)]]-3-[[[[1-(2-Amino-4-thiazolyl)-2-[(2-methyl-4-oxo-1-sulfo-3-azetidinyl)amino]-2-oxoethylidene]amino]oxy]methyl]-6,7-dihydroxy-2-quinoxalinecarboxylic acid

EXAMPLE 20A 6,6-Dimethyl[1,3]dioxolo[4,5-f]-2,1,3-benzoxadiazole, 1-oxide 133 g of 2,2-Dimethyl-5,6-dinitro-1,3-benzodioxole was dissolved in 1200 ml dimethylsulfoxide and 39.9 g sodium azide was added and the mixture was stirred at 85°–90° C. for 4 hours. After cooling down to room temperature, the dark solution was poured into 3 L ice water. A precipitate of the title compound was immediately formed. It was isolated by filtration, washed with ice water, redissolved in ethyl acetate (5 L) and dried over $Na_2SO_4$. After removal of the solvent in vacuo 115.7 g of title compound were recovered as yellow needles. M.P. 185°–187° C.

$^1$H-NMR(DMSO-d$_6$) δ=1.71 (s, 6H); 6.79 (s, 1H); 7.04 (s, 1H) ppm.

EXAMPLE 20B 2,2,7-Trimethyl-1,3-dioxolo[4,5g]quinoxaline-6-carboxylic acid, 1,1-dimethylethyl ester, 5,8-dioxide To 32 g of the compound of Example 20A and 4.75 g of tert-butyl acetoacetate in 750 ml ethanol were added slowly 155 ml of a 1N solution of NaOH (solid) in ethanol (abs.). The temperature of the reaction mixture rose from room temperature to ~40° C. After complete addition of the NaOH the temperature was kept at 50°–60° C. with heating for 45 minutes. A yellow precipitate was formed. After cooling with ice the precipitate was isolated by filtration and washed with ice water. Drying over $P_2O_5$ gave pure title compound 43.6 g yellow needles.

M.P. 205°–207° C. (from toluene). $^1$H-NMR(DMSO-d$_6$): δ=1.55 (s, 9H); 1.76 (s, 6H); 2.31 (s, 3H); 7.65 (s, 1H); 7.73 (s, 1H) ppm. IR(KBr): 1740 cm$^{-1}$(COO+).

EXAMPLE 20C

7-[(Trifluoroacetyloxy)methyl]-2,2-dimethyl-1,3-dioxolo-[4,5g]quinoxaline-6-carboxylic acid, 1,1-dimethyl ethyl ester, 5-oxide To 20 g of the compound of Example 20B suspended in 60 ml dichloromethane was added at −20° C. a solution of 100 ml trifluoroacetic acid anhydride in 40 ml dichloromethane. While stirring, an orange colored solution was obtained after 30 minutes. The solution was then stirred at 0° C. for one hour. The color turned to a dark green. The solvent, excess trifluoroacetic acidanhydride and formed trifluoroacetic acid was then distilled of in vacuo at room temperature. After evaporation with an oil-vacuo for additional one hour a beige foam was obtained. This was stirred with 150 ml ether and cooled to −20° C. A dark red suspension was obtained. After filtration and washing with ether and hexane the title compound was obtained as a beige solid (20.4 g). The compound is unstable and must be immediately used for further transformation.

EXAMPLE 20D 7-(Bromomethyl)-2,2-dimethyl-1,3-dioxolo-[4,5g]quinoxaline-6-carboxylic acid, 1,1-dimethylethyl ester, 5-oxide 16 g of crude 7-[(Trifluoroacetyloxy)methyl]-2,2-dimethyl-1,3-dioxolo-[4,5g]quinoxaline-6-carboxylic acid, 1,1-dimethyl ethyl ester, 5-oxide and 7 g lithium bromide was stirred at 50° C. for 3 hours in 750 ml acetone. After continued stirring at room temperature overnight, the solvent was distilled off and the residue suspended in toluene/ethyl acetate (6:1) and after filtration the filtrate passed through a column with 500 g silica gel. Toluene/ethyl acetate (6:1) as an eluent. From the relevant fractions 14.7 g pure title compound was obtained after evaporation as a white crystalline solid.

M.P.=196°-198° . IR(KBr): 1735 cm$^{-1}$ (COO+)
$^1$H-NMR(DMSO-d$_6$): $\delta$=1.62 (s, 9H); 1.77 (s, 6H); 4.60 (s, 2H); 7.21 (s, 1H); 7.77 (s, 1H) ppm.

EXAMPLE 20E

7-[[[Bis[(1,1-dimethylethoxy)carbonyl]amino]oxy]methyl]-2,2-dimethyl-1,3-dioxolo[4,5g]-quinoxaline-6-carboxylic acid, 1,1-dimethylethyl ester, 5-oxide A mixture of the title compound of Example 20D (2.05 g), and the title compound of Example 6 (1.4 g) and potassium carbonate (powder) (7.1 g) and acetone (100 ml) was stirred for 3 hours at room temperature. The solvent was distilled off and the residue was taken up in a mixture of water and ethyl acetate. The washed organic phase was concentrated and purified by chromatography on silica gel eluting with toluene/ethyl acetate (3:1). Fractions containing the title compound were collected and evaporated. Yield 2.60 g; m.p.=122°-124° C. (light yellowish solid).

$^1$H-NMR(DMSO-d$_6$): $\delta$=1.29 (s, 18H); 1.50 (s, 9H); 1.81 (s, 6H); 4.93 (s, 2H); 7.40 (s, 1H) ppm.

EXAMPLE 20F

7-[(Aminooxy)methyl]-2,2-dimethyl-1,3-dioxolo-[4,5g]quinoxaline-6-carboxylic acid, 1,1-dimethylethyl ester, hydrobromide The title compound of Example 20E (0.563 g) was dissolved in dry dichloromethane (20 ml) and at −70° C. boron tribromide (2 ml) was added. Stirring was continued for 2 hours at −70° C. and at room temperature overnight. After evaporation in vacuo the brown honey like residue was dissolved in 25 ml ethyl acetate/methanol at −80° C., stirred for 10 minutes and again evaporated. The residue was stirred with warm n-hexane. The yellow solid was used in the next step without further purification. Yield: 0.32 g.

EXAMPLE 20G

3-[(Aminooxy)methyl]-6,7-dihydroxy-2-quinoxaline-6-carboxylic acid, hydrochloride The compound from Example 20F (0.3 g) was stirred with hydrochloric acid conc. (3 ml) at 65°-70° C. for 1 hour. A yellow precipitate of the title compound was formed. It was isolated by filtration and dried over P$_2$O$_5$ in vacuo for 8 hours. Yield: 0.25 g.

EXAMPLE 20H

Alternate method for preparing the title compound of Example 11

[2R-[2$\alpha$,3$\alpha$(Z)]]-3-[[[[1-(2-Formylamino-4-thiazolyl)-2-[(2-methyl-4-oxo-1-sulfo-3-azetidinyl)amino]-2-oxoethylidene]amino]oxy]methyl]-6,7-dihydroxy-2-quinoxalinecarboxylic acid, tetrabutylammonium salt (1:2)

2.1 g of (2R-cis)-3-[[[2-(Formylamino)-4-thiazolyl]-oxoacetyl]amino]-2-methyl-4-oxo-1-azetidine-sulfonic acid, N,N,N-tributyl-1-butanammonium salt (Example 7) were stirred in 80 ml water until complete solution (~1 h). 0.55 g tetrabutylammoniumhydrogensulfate were added and the pH of the solution was adjusted to DH 2.0 (1n HCL). 1.2 g of the compound of Example 9 were divided in 6 portions. Every 20 minutes one portion was added slowly to the solution and after each addition the pH was readjusted to 2.0 (TBA+OH−). The reaction solution was stirred for two additinal hours after the last addition of the compound of Example 9 and the pH was controlled every 20 minutes and readjusted to 2.0 if necessary. The reaction was stopped by adjusting the pH to 6.5 (TBA+OH[31]) and the remaining solution freeze dried. 12–13 g solid material of the crude title compound was obtained which was purified by column chromatography.

EXAMPLE 20I

[2R-[2$\alpha$,3$\alpha$(Z)]]-3-[[[[1-(2-Amino-4-thiazolyl)-2-[(2-methyl-4-oxo-1-sulfo-3-azetidinyl)amino]-2-oxoethylidene]amino]oxy]methyl]-6,7-dihydroxy-2-quinoxaline-carboxylic acid 8.7 of the purified compound of Example 20H freeze-dried material were stirred for one hour in 400 ml ethyl acetate to get a uniform crystalline material. This material was dissolved in 1 L water and 470 tetrahydrofuran and stirred to complete solution. The pH was then adjusted to 0.5 with concentrated hydrochloric acid and the solution stirred for 3 days at room temperature. After ~8 hours crystals of the title compound were formed. On the third day the formed title compound was isolated by filtration and washed with tetrahydrofuran/water (1:10) containing a few drops of 1n hydrochloric acid. After drying over P$_2$O$_5$ in vacuo a solid mass of title compound was obtained. This was stirred with 100 ml tetrahydrofuran containing 3 drops water for one hour. After filtration 4.2 g of the title compound light yellowish needles were obtained (drying over silica gel for 6 hours). Purity 99.5% (by HPLC)

M.P. dec >208° C.

EXAMPLE 21

Alternate Method for Preparing 2,2,7-Trimethyl-1,3-dioxolo[4,5g]quinoxaline-6-carboxylic acid, 1,1-dimethylethyl ester To 38 g of the compound of Example 20B dissolved in 100 ml CHCl$_3$ (abs.) was added 75 g PCl$_3$ dropwise. During adding, the temperature rose to 40° C. (about 40 minutes). Stirring was then continued overnight at room temperature. Formed POCl$_3$, solvent and excess PCl$_3$ were then distilled off in vacuo. The oily residue was dissolved in 250 ml ethyl acetate and stirred with ice water for 30 minutes while the pH was adjusted with sodium bicarbonate between 6–7. The separated organic phase was then washed with water, dried and the solvent distilled off. 33 g pure title compound was obtained as white crystal solid.

EXAMPLE 22

Alternate Preparation of 2,2,7-Trimethyl-1,3-dioxolo[4,5g]quinoxaline-6-carboxylic acid, 1,1-dimethylethyl ester, 5,8-dioxide To a solution of 2,2,7-Trimethyl-1,3-dioxolo[4,5g-]quinoxaline-6-carboxylic acid, 1,1-dimethylethyl ester (1.26g, 4.0 mmol) in 20 ml chloroform was added 2.53 g (8.8 mmol) m-chloroperoxybenzoic acid. After stirring overnight at room temperature a solid was filtered off and the solvent was distilled off in vacuo. The residue was partitioned between water and ethyl acetate. The phases were separated and the organic phase washed with saturated sodium hydrogencarbonate solution and with brine. After drying over sodium sulfate and evaporation 1.41 (quant.) of a mixture of the title compound and 2,2,7-Trimethyl-1,3-dioxolo-[4,5g]-quinoxaline-6-carboxylic acid, 1-dimethyl ester, 8-oxide was obtained. The mixture was chromatographed on silica gel with ethyl acetate/petroleum ether 1:2 as eluent to give 0.41 g (30.8%) mono-N-oxide and 0.82 g (58.9%) di-N-oxide. M.P.: 181.9° C.

IR(KBr): 1735 cm$^{-1}$ (CO) $^1$H-NMR(DMSO-d$_6$): δ=1.59 (s, 9H); 1.80 (s, 6H); 2.40 (s, 3H); 7.68 (s, 1H); 7.73 (s, 1H); ppm Using the procedure above with four equivalents of MCPBA afforded the di-N-oxide in 70% yield.

EXAMPLE 23

7-Bromomethyl-2,2-dimethyl-1,3-dioxolo-[4,5g]-quinoxaline-6-carboxylic acid, 1,1-dimethylethyl ester, 5,8,-dioxide To a solution of the title compound of Example 22 (3.48 g, 10.0 mmol) in 20 ml carbon tetrachloride were added 1.78 g (10.0 mmol) N-bromo succinimide. The mixture was heated to reflux and 10 portions of catalytical amounts of azobisisobutyronitrile were added within 8 hours. The mixture was heated overnight and after cooling the solid filtered off with suction. The filtrate was evaporated and the residue (3.7 g, 87%) chromatographed on silica gel with ethyl acetate/petroleum ether 1:1 as eluent to give 1.87 g (43.6%) of the title compound.

M.P.: 150.9° C. IR(KBr): 1740 cm$^{-1}$ (CO) $^1$H-NMR(DMSO-d$_6$): δ=1.60 (s, 9H); 1.81 (s, 6H); 4.62 (s, 2H); 7.73 (s, 1H); 7.79 (s, 1H); ppm.

EXAMPLE 24

7-[[[Bis[1,1-dimethylethoxy)carbonyl]amino]oxy]methyl]-2,2-dimethyl-1,3-dioxolo[4,5g]-quinoxaline-6-carboxylic acid, 1,1-dimethylethyl ester, 5,8-dioxide To a solution of the title compound of Example 23 (1.81 g, 4.25 mmol) in 30 ml acetone were added 2.35 g (17.0 mmol) potassium carbonate, the title compound of Example 6 (0.97g, 4.16 mmol) and a catalytical amount of sodium iodide. The mixture was stirred for 60 hours at room temperature. The resulting solid was filtered off with suction, washed with acetone, dissolved in ethyl acetate and washed with water, dil. citric acid and again water. After drying and evaporation of the solvent the residue was dissolved in 10 ml ether and an equal amount of petroleum ether was added. After one night in the refrigerator the resulting precipitate was filtered off, washed with petroleum ether and dried to give 2.1 g (85.1%) of the title compound.

M.P.: 75.5° C. IR(KBr): 1740, 1790 cm$^{-1}$ (CO) $^1$H-NMR(DMSO-d$_6$): δ=1.29 (s, 18H), 1.55 (s, 9H); 1.81 (s, 6H); 5.06 (s, 2H); 7.78 (s, 1H); 7.80 (s, 1H); ppm.

EXAMPLE 25

5,6-Bis(phenylmethoxy)benzofurazan, 1-oxide

To a solution of 4,5-dibenzyloxy-1,2-dinitrobenzene, (1.9 g, 5.0 mmol) in 25 ml dimethylsulfoxide were added 1.16 g (17.8 mmol) sodium azide and the mixture was stirred at 85° C. for 4 hours. The mixture was then poured into water and the resulting precipitate filtered off with suction, washed with water and dried in vacuo. Yield of title compound 1.49 g (85.5%)

M.P.: 206°-208° C. (dec.) $^1$H-NMR(DMSO-d$_6$: δ=5.28 (s, 4H), 7.2-7.6 (m, 12H); ppm.

EXAMPLE 26

3-Methyl-6,7-bis(phenylmethoxy)-2-quinoxaline-carboxylic acid, ethyl ester, 1,4-dioxide To a suspension of the title compound of Example 25 (1.04 g, 3.0 mmol) in 20 ml ethanol were added at 60° C. ethyl acetoacetate (0.78 g, 6.0 mmol) and sodium hydroxide (0.12 g, 3.0 mmol ) in 4 ml ethanol. The mixture was stirred at 60° C. for 8 hours and another 10 hours at room temperature. The resulting precipitate was filtered off with suction, washed with water and dried in vacuo to give 0.62 g of crude product. The crude material was chromatographed on silical gel with ethyl acetate/petroleum ether 2:1 as eluent and yielded 0.38 g (27.5 %) of the title compound.

M.P.: 175°-177° C. (dec.) IR(KBr): 1740 cm$^{-1}$ (CO) $^1$H-NMR(DMSO-d$_6$): δ=1.34 (t,3H); 2.40 (s, 3H); 4.48 (q, 2H); 5.42 (s, 4H); 7.3-7.6 (m, 10H); 7.82 (s, 1H); 7.91 (s, 1H); ppm.

EXAMPLE 27

3-Methyl-6,7-bis(phenylmethoxy)quinoxaline-2-carboxylic acid

EXAMPLE 27A

3-Methyl-6,7-bis(phenylmethoxy)quinoxaline-2-carboxylic acid, phenylmethyl ester The compound from Example 2 (6.3 g; 20.0 mmol) was treated with concentrated hydrochloric acid (170 ml) at 75° C. for 90 minutes and the formed precipitate was collected from the cold suspension by suction. After drying in vacuo over P$_2$O$_5$ and subsequent washing with acetonitrile, ether and n-pentane, this crude hydrochloride salt (4.0g; mp 201°-202° C.) was suspended in dry dimethylformamide (50 ml) and then potassium carbonate (12.4 g; 0.09 mol) was added slowly (evolution of CO$_2$) followed by the addition of benzylbromide (15.4 g; 0.09 mol). After being stirred at 75° C. for 4 hours the mixture was cooled, filtered and the filtrate was evaporated in vacuo. The resulting residue was washed with few ml ether and then taken up in ethyl acetate and water and the pH of the mixture was adjusted to 2 by the addition of diluted hydrochloric acid. The organic layer was separated, washed with water and brine, dried (Na$_2$SO$_4$) and evaporated in vacuo to leave a residue which was crystallized from ethylacetate and petroleum ether, yield: 3.8 g (39%) mp 137°-139° C.

IR(KBr): 1715, 1703 cm$^{-1}$; $^1$H-NMR(DMSO-d$_6$): δ=2.78 (s, 3H); 3.33 (s, 2H); 5.37 (s, 2H); 5.43 (s, 2H); 7.25–7.65 (m, 17H) ppm.

EXAMPLE 27B

3-Methyl-6,7-bis(phenylmethoxy)quinoxaline-2-carboxylic acid

The compound of Example 27A (4.9 g, 10.0 mmol) was added to a solution of potassium hydroxide (2.2 g, 40.0 mmol) in ethanol/water (80 ml/16 ml) and the mixture was stirred at 80° C. for 20 hours and then cooled (5° C.). The precipitate was collected by suction, washed with ether (4.3 g) and then suspended in water (100 ml). After correction of the pH of this suspension to 2 by the addition of 2N HCl stirring was continued at room temperature for 20 minutes and the crystallized title compound was isolated by suction, washed with water and dried in vacuo over P$_2$O$_5$. Yield: 3.4 g (85%); mp 198°–200° C. C$_{24}$H$_{20}$N$_2$O$_4$.0.1 H$_2$

| | C$_{24}$H$_{20}$N$_2$O$_4$.0.1 H$_2$O | |
|---|---|---|
| | calc. (%) | found (%) |
| C | 71.67 | 71.50 |
| H | 5.06 | 5.03 |
| N | 6.96 | 7.14 |

IR(KBr): 1752, 1717 cm$^{-1}$; $^1$H-NMR(DMSO-d$_6$): δ=2.78 (s, 3H); 4.39 (s, 4H); 7.25–7.70 (m, 12H); COOH too broad, not registered.

EXAMPLE 28

4-Bis(phenylmethoxy)-1,2-benzenediamine, triflouroacetate (1:1) salt

EXAMPLE 28A 2,2-Dimethyl-N-[2-nitro-4,5-bis(phenylmethoxy)methoxy)phenyl]propanamide To a suspension of 2-nitro-4,5-dibenzyloxybenzoic acid (1.89, 5.0 mmol) in 30 ml tert-butanol were added diphenylphosphoryl azide (1.65 g, 6.0 mmol) and triethylamine (0.61 g, 6.0 mmol). The mixture was heated to reflux overnight. After cooling the resulting precipitate was filtered off, washed with ether and dried in vacuo.

Yield of title compound: 1.74 g (84%) m.p.: 145°–149° C. IR(KBr): 1715 cm$^{-1}$ (CO). $^1$H-NMR(DMSO-d$_6$): δ=1.47 (s, 9H); 5.19 (s,2H); 5.22 (s, 2H); 7.40 (mc, 10H); 7.70 (s, 1H); 7.73 (s, 1H); 9.65 (s, 1H); ppm.

EXAMPLE 28B

N-[2-Amino-4,5-bis(phenylmethoxy)phenyl]-2,2-dimethylpropanamide

Under nitrogen, the title compound of Example 28A (15.77 g, 35.0 mmol) was dissolved in 350 ml dimethylformamide. 500 mg platinum (IV) oxide were added, the mixture was heated to 60° C. and hydrogenated by monitoring with thin layer chromatography until the end of the reaction (1–5 days). The hydrogen was replaced with nitrogen, the catalyst was filtered off and the filtrate evaporated (all operations under nitrogen, otherwise the product has a deep blue color). The residue was triturated with degassed water to remove residual dimethylformamide.

Yield after drying of title compound: 14.1 g (96%) m.p. 115° C. IR(KBr): 1680 cm$^{-1}$ (CO). $^1$H-NMR(DMSO-d$_6$): δ=1.45 (s, 1H); 4.60 (s, broad, 2H); 4.91 (s, 2H); 5.00 (s, 2H); 6.50 (s, 1H); 6.94 (s, 1H); 7.40 (mc, 10H); 8.20 (s, 1H);ppm.

EXAMPLE 28C

4-Bis(phenylmethoxy)-1,2-benzenediamine, trifluoroacetate (1:1) salt

A mixture of the title compound of Example 28B (1.0 g, 2.38 mmol) and 20 ml of trifluoroacetic acid was stirred at 0° C. for one hour. Trifluoroacetic acid was distilled off and the residue triturated with ether. The title compound was filtered off, washed with water and dried in vacou.

Yield 0.78 g (74%) M.P.: 122.5° C. C$_{20}$H$_{20}$N$_2$O$_2$. 1:1 CF$_3$COOH

| | C$_{20}$H$_{20}$N$_2$O$_2$.1:1 CF$_3$COOH | |
|---|---|---|
| | Calculated (%) | Found (%) |
| C | 60.31 | 59.94 |
| H | 4.82 | 4.83 |
| N | 6.37 | 6.53 |
| F | 13.60 | 13.60 |

IR(KBr): 1675cm$^{-1}$ (CO). $^1$H-NMR(DMSO-d$_6$): δ=5.03 (s, 4H); 6.79 (s, 2H); 7.41 (mc, 10 H); ppm.

EXAMPLE 29

3-Methyl-6,7-bis(phenylmethoxy)-2-quinoxalinecarboxylic acid, 1,1-dimethylethyl ester 4,5-Bis(phenylmethoxy)-1,2-benzenediamine, trifluoroacetate (1:1) salt (5.48 g, 12.62 mmol) was dissolved in 45 ml water/tetrahydrofuran (2:1) and the pH was brought to 5 with 2N sodium hydroxide solution. t-Butyl 2,3-dioxobutynate (3.44 g, 20.0 mmol) was added and the mixture was heated to reflux for 80 minutes. Tetrahydrofuran was distilled off and the residue was extracted with ethyl acetate. The organic phase was washed with water, dried and stirred with activated carbon. After filtration and evaporation a resin was obtained which crystallized. This material was chromatographed on silica gel with ethyl acetate/petroleum ether (1:2) as eluent. The sample containing fractions were collected to give after evaporation and trituration with petroleum ether 3.33 g (58%) of the title compound.

M.P.: 111° C. IR(KBr): 1725 cm$^{-1}$ (CO). $^1$H-NMR(DMSO-d$_6$): δ=1.45 (s, 9H); 2.67 (s, 3H); 5.32 (s, 4H); 7.2–7.6 (m, 12 H); ppm.

EXAMPLE 30

[2R-[2α,3α(Z)]]-3-[[[[1-(2-Amino-4-thiazoly)-2-[(2-methyl-4-oxo-1-sulfo-3-azetidinyl)amino]-2-oxoethylidene]amino]oxy]methyl]-6,7-dihydroxy-2-quinoxalinecarboxylic acid, L-arginine salt To 22 gram of the title compound of Example 11 ([2R-[2α,3α(Z)]]-3-[[[[1-(2-amino-4-thiazolyl)-2-[(2-methyl-4-oxo-1-sulfo-3-azetidinyl)amino]-2-oxoethylidene]amino]oxy]methyl]-6,7-dihydroxy-2-quinoxalinecarboxylic acid) activity was added 12.5 grams of L-arginine and the two powders were mixed. The powder blend was added to 180 grams of water with vigorous agitation until the powders were dissolved. The DH of the solution was adjusted to 5.5 with an additional 0.9 grams of L-arginine to the solution. The final batch volume was adjusted to 220 mL with addition of more water. The solution was filtered through a 0.2 micron filter into appropriate containers and freeze dried. The resultant product was a dark yellow to orange cake or fragmented cake.

What we claim is:

1. A compound of the formula

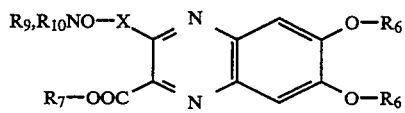

wherein R_6/R_6 is C(CH_3)_2 taken together with the oxygen atoms to which they are attached forming a 5-membered dioxolane ring, R_7 is tert-butyl; R_9 and R_10 are BOC(t-butoxy-carbonyl) and X is —(CH_2)_n— wherein n is one, two, three or four.

2. A compound of the formula

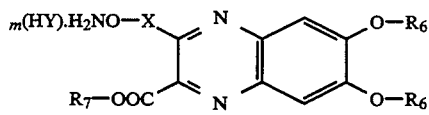

wherein R_6 and R_7 is hydrogen, (HY) is HCl and X is —(CH_2)_n— wherein n is one, two, three or four.

3. A compound according to claim 2, 3-[(Aminooxy)methyl]-6,7-dihydroxy-2-quinoxalinecarboxylic acid, monohydrochloride.

4. A compound according to claim 2, 3-[2-(Aminooxy)ethyl]-6,7-dihydroxy-2-quinoxaline-2-carboxylic acid hydrochloride.

5. A compound according to claim 2, 3-[3-(Aminooxy)propyl]-6,7-dihydroxy-2-quinoxalinecarboxylic acid, hydrochloride.

6. A compound according to claim 2, 3-[4-(Aminooxy)butyl]-6,7-dihydroxy-2-quinoxaline-2-carboxylic acid, hydrochloride.

7. A compound of the formula

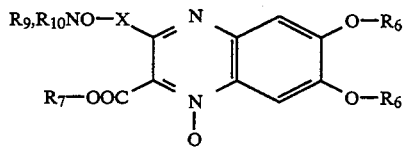

wherein R_6/R_6 is C(CH_3)_2 taken together with the oxygen atoms to which they are attached forming a 5-membered dioxolane ring, R_7 is tert-butyl; R_9 and R_10 are BOC(t-butoxy-carbonyl) and X is —(CH_2)_n— wherein n is one, two, three or four.

* * * * *